United States Patent
San et al.

(10) Patent No.: US 9,309,543 B2
(45) Date of Patent: Apr. 12, 2016

(54) BACTERIA AND METHOD FOR SYNTHESIZING FATTY ACIDS

(75) Inventors: Ka-Yiu San, Houston, TX (US); Mai Li, Houston, TX (US); Xiujun Zhang, Houston, TX (US)

(73) Assignee: William Marsh Rice University, Houston, TX (US)

( * ) Notice: Subject to any disclaimer, the term of this patent is extended or adjusted under 35 U.S.C. 154(b) by 468 days.

(21) Appl. No.: 13/635,867

(22) PCT Filed: Mar. 18, 2011

(86) PCT No.: PCT/US2011/028983
§ 371 (c)(1),
(2), (4) Date: Nov. 27, 2013

(87) PCT Pub. No.: WO2011/116279
PCT Pub. Date: Sep. 22, 2011

(65) Prior Publication Data
US 2014/0093921 A1      Apr. 3, 2014

Related U.S. Application Data

(60) Provisional application No. 61/315,188, filed on Mar. 18, 2010, provisional application No. 61/315,139, filed on Mar. 18, 2010, provisional application No. 61/321,262, filed on Apr. 6, 2010, provisional application No. 61/332,917, filed on May 10, 2010, provisional application No. 61/436,078, filed on Jan. 25, 2011.

(51) Int. Cl.
*C12N 15/00* (2006.01)
*C12N 1/20* (2006.01)
*C12P 7/64* (2006.01)
*C12N 9/16* (2006.01)

(52) U.S. Cl.
CPC ............... *C12P 7/6409* (2013.01); *C12N 9/16* (2013.01); *C12Y 301/02014* (2013.01); *Y02P 20/52* (2015.11)

(58) Field of Classification Search
CPC .................................. C12N 15/00; C12N 1/20
USPC .................................. 435/69.1, 252.3, 320.1
See application file for complete search history.

(56) References Cited

PUBLICATIONS

Davies, H.M., L. Anderson, J. Bleibaum, D.J. Hawkins, C. Fan, A.C. Worrell, and T.A. Voelker. 1993. Fatty acid synthesis genes: Engineering the production of medium chain fatty acids. p. 176-181. In: J. Janick and J.E. Simon (eds.), New crops. Wiley, New York.
Lu, X., H. Vora and C. Khosla. 2008. "Overproduction of free fatty acids in *E. coli*: Implications for biodiesel production." Metabolic Engineering. 10: 333-339.
Chin, J.W., Khankal, R., Monroe, C.A., Maranas, C.D., Cirino, P.C., 2009. "Analysis of NADPH supply during xylitol production by engineered *Escherichia coli*." Biotechnol. Bioeng. 1 02(1 ):209-20.
Sanchez, A.M., Andrews, J., Hussein, I., Bennett, G.N., San, K.Y. 2006. "Effect of overexpression of a soluble pyridine nucleotide transhydrogenase (UdhA) on the production of poly(3-hydroxybutyrate) in *Escherichia coli*." Biotechnol. Prog. 22(2):420-5.

*Primary Examiner* — Maryam Monshipouri
(74) *Attorney, Agent, or Firm* — Boulware & Valoir

(57) ABSTRACT

There is provided a recombinant bacterium comprising at least one overexpressed acyl-ACP thioesterase gene, and wherein at least one gene from the tricarboxylic acid cycle or glycolysis or both is inactivated. There is also provided a method for producing fatty acids, said method comprising culturing bacteria comprising at least one overexpressed acyl-ACP thioesterase gene in a growth medium in a container having walls; allowing said bacteria to secrete fatty acids; and collecting said fatty acids. Acid supplementation is also shown to increase productivity.

8 Claims, 6 Drawing Sheets

No Acetic acid – 2 days

No acetic acid – 5 days plus acetic acid – 5 days plus acetic acid – 5 days

BACTERIA AND METHOD FOR SYNTHESIZING FATTY ACIDS

PRIOR RELATED APPLICATIONS

This invention claims priority to U.S. 61/315,139 entitled "Fatty Acid Synthesis in Bacteria" and U.S. 61/315,188 entitled "Method of Producing Fatty Acid From Bacteria" which were filed Mar. 18, 2010, U.S. 61/321,262 entitled "Method to Improve Fatty Acid Production" which was filed Apr. 6, 2010, U.S. 61/332,917 entitled "Improved Fatty Acid Production by Acid Supplementation" which was filed May 10, 2010, and U.S. 61/436078 entitled "Fatty Acid Production in Bacteria" which was filed Jan. 25, 2011. This invention also claims priority to PCT/US2011/028983 entitled "BACTERIA AND METHOD FOR SYNTHESIZING FATTY ACIDS" which was filed Mar. 18, 2011. Each of these patent applications is incorporated by reference in its entirety.

FEDERALLY SPONSORED RESEARCH STATEMENT

"This invention was made with government support under grant number EEC-0813570 awarded by the National Science Foundation. The government has certain rights in the invention."

FIELD OF THE INVENTION

The invention relates to the production of fatty acid by genetically engineered microorganisms, in particular to engineered microorganisms that produce large amounts of free fatty acids by virtue of the addition of, for example, a plant acyl-ACP thioesterase and/or deactivation of at least one gene from the tricarboxylic acid cycle. Methods of improved fatty acid production using microorganisms are also provided.

BACKGROUND OF THE INVENTION

Increasing energy costs and environmental concerns have emphasized the need to produce sustainable renewable fuels and chemicals. Fatty acids are composed of long alkyl chains and represent nature's "petroleum," being a primary metabolite used by cells for both chemical and energy storage functions. These energy-rich molecules are today isolated from plant and animal oils for a diverse set of products ranging from fuels to oleochemicals.

Whereas microbial fermentation processes for producing ethanol and related alcohol biofuels are well established, biodiesel (methylesters of fatty acids) is the major long chain product produced biologically, and it is almost exclusively derived from plant oils today. However, slow cycle times for engineering oil seed metabolism and the excessive accumulation of glycerol as a byproduct are two major drawbacks of deriving biodiesel from plants. Although most bacteria do produce fatty acids as cell envelope precursors, the biosynthesis of fatty acids is tightly regulated at multiple levels and large quantities are not made. Thus, the production of fatty acids from bacteria has not yet reached the point where it is cost effective.

By introducing four distinct genetic changes into the *E. coli* genome, Lu et al. engineered a more efficient producer of fatty acids. Lu (2008). Their bacteria comprised (a) knocking out the endogenous fadD gene (encoding a fatty acyl-CoA synthetase) in order to block fatty acid degradation; (b) heterologous expression of a plant thioesterase to increase the abundance of shorter chain fatty acids with an eye towards improving fuel quality; (c) increasing the supply of malonyl-CoA by over-expressing ACC (acetyl-CoA carboxylase) and (d) releasing feedback inhibition caused by long-chain fatty acyl-ACPs through over-expression of an endogenous thioesterase.

Although a promising start, the authors acknowledge that considerable improvement to this strain must be made before commercial viability is attained. Furthermore, the authors obtained the fatty acids by spinning down the cells, lysing them, and extracting the fatty acids, thus the cells could not be further used for synthesis of fatty acids, further reducing the cost effectiveness of the method.

Therefore, there is a need in the art for a biological system of producing fatty acids that is more efficient and cost effective than heretofore realized. A more scalable, controllable and economic route to this important class of chemicals would be through the microbial conversion of renewable feedstocks, such as biomass-derived carbohydrates. Here we demonstrate the engineering of *Escherichia coli* to produce tailored fatty acids directly from simple sugars. Further, since the enzymes and pathways are well know, the methodology can be applied to other microorganisms, such as yeast or other species of bacteria.

SUMMARY OF THE INVENTION

The invention generally relates to engineered microorganisms that can produce at least about 50% more fatty acids that the corresponding non-engineered control bacteria, wherein said microorganisms comprise a thioesterase reduction or complete inactivation of one or more proteins in the TCA cycle or glycolysis, or both. The thioesterase can be from any species and is selected to have the desired specificity. Alternatively, a hybrid TE can be used, as described herein. We have exemplified several variations of TE herein.

The TCA enzymes that can be reduced or inactivated include aconitase, isocitrate dehydrogenase, α-ketoglutarate dehydrogenase, succinyl-coA synthetase, succinic dehydrogenase, fumarase, malate dehydrogenase, and citrate synthase. In preferred embodiments the microorganism comprises inactivated succinyl-coA synthetase. In other embodiments, the organism is *E. coli* and the mutated TCA gene is the sucC gene, which encodes the succinyl-CoA synthetase beta subunit.

Glycolytic enzymes include hexokinase (aka glucokinase), phosphoglucose isomerase, phosphofructokinase, aldolase, triose phosphate isomerase, glyceraldehyde-3-phosphate dehydrogenase, phophoglycerate kinase, phophoglycerate mutate, enolase, pyruvate kinase, and the transport enzymes for glucose uptake, such as glucose phophotransferase (aka glucose permease).

Glucokinase and glucose phophotransferase are particularly preferred. In other embodiments, the organism is *E. coli* and the mutated glycolytic gene is pstG or glk.

Other mutations that can be combined therewith include of i) overexpressed coenzyme A-acyl carrier protein transacylase, ii) overexpressed transhydrogenase, iii) moderately overexpressed acetyl-CoA carboxylase, and iv) reduced activity of endogenous fatty acyl-CoA synthetase.

Particularly preferred genotypes include:

| | |
|---|---|
| ΔfadD, ΔsucC and TE⁺ | ΔsucC and TE⁺ |
| ΔfadD, ΔfumAC and TE⁺ and optional ΔsucC | ΔfumAC and TE⁺ and optional ΔsucC |
| ΔfadD, ΔgapA and TE⁺ and optional ΔsucC | ΔgapA and TE⁺ and optional ΔsucC |
| ΔfadD, ΔptsG and TE⁺ and optional ΔsucC | ΔptsG and TE⁺ and optional ΔsucC |
| ΔfadD, ΔpfkA and TE⁺ and optional ΔsucC | ΔpfkA and TE⁺ and optional ΔsucC |
| ΔfadD, Δglk and TE⁺ and optional ΔsucC | Δglk and TE⁺ and optional ΔsucC |
| TE⁺ and fabD⁺ | TE⁺ and NADP-kinase⁺ |
| TE⁺ and udhA⁺ | acc⁺ and/or fabD⁺ and/or udhA⁺ and/or NAD-kinase⁺ combined with any genotypes in this table |
| hybrid TE⁺, wherein the hybrid TE⁺ can be used alone or can replace any TE⁺ in this table | hybrid TE⁺ comprising amino or carboxy (or both) terminal TE from Ricinus communis coupled to the carboxy or amino (or both) terminal of TE from another species, wherein the hybrid TE⁺ can be used alone or replace any TE⁺ in this table |

Another invention is a hybrid acyl-ACP thioesterase from oil-producing plants. By domain swapping an amino terminal domain with the preferred specificity and by making other modifications to the added thioesterases, we can make tailored enzymes that produce particular fatty acid profiles. In particular, terminal regions from the thioesterase of *Ricinus communis* (Castor bean) is highly active in our system, but we have exemplified many species and variants thereof.

We can also further increase fatty acid synthesis by combining hybrid TE's with reducing or deleting one or more genes from glycolysis, TCA, or both.

We have now surprisingly discovered that such microorganisms release large quantities of fatty acids that tend to clump or stick to the vessel walls, where they can be easily collected as solids or dissolved in hydrophobic solvents or alkali solutions.

In another embodiment of the invention, we can further enhance fatty acid production when the growth media is supplemented with an acid, such as hydrochloric acid (HCl) or acetic acid ($CH_3COOH$). A preferred range is more than 0.1% and less than 1% (0.1-1%).

We have exemplified this aspect of the invention by decanting the cells and collecting the fatty acids from the walls of a flask using chloroform, but large scale systems can easily include specialized vessels containing baffles therein for providing additional surface area for collection of fatty acids. Furthermore, it may be possible to establish a closed loop system that circulates cells through a such a vessel for secretion of fatty acids, then holds the cells in another vessel or portion of the system pending collection of solid fatty acid or extraction of fatty acids and removal of all solvents, and then reseeds that vessel with the same cells to repeat the cycle. It may also be possible to collect the fats by filtration, leaving cells behind.

In particular, this application provides a recombinant bacterium, preferably *E. coli*, comprising at least one overexpressed acyl-ACP thioesterase gene, and wherein at least one gene from the tricarboxylic acid cycle or glycolysis or both is inactivated.

In some embodiments, at least one acyl-ACP thioesterase gene is from a plant, for example overexpressed acyl-ACP thioesterase gene from *Ricinus communis, Jatropha curcas, Diploknema butyracea, Cuphea palustris* or *Gossypium hirsutum*, or an overexpressed hybrid acyl-ACP thioesterase comprising different thioesterase domains operably fused together. Preferably, the hybrid thioesterase includes a terminal region of the acyl-ACP thioesterase from *Ricinus communis* or a 70, 80, 90 or 95% homolog thereto operably coupled to the remaining portion of the thioesterase from another species.

In particular, the microorganism can comprise an overexpressed hybrid acyl-ACP thioesterase comprising the amino terminal region of the thioesterase from *Ricinus communis* operably coupled to the carboxyl region of the thioesterase from another species. Such microorganisms can be combined with each of the other mutations and overexpressions described herein.

In other embodiments, this application provides a recombinant microorganism that overexpresses both an acyl-ACP thioesterase gene and a transhydrogenase gene, for example encoding a soluble pyridine nucleotide transhydrogenase (e.g., udhA) and/or overexpressed NAD-kinase (e.g., NAD-kinase⁺) and/or a moderately overexpressed acetyl-CoA carboxylase (e.g., acc). The microorganism can further comprise an inactive or knockout Acyl-CoA synthase (e.g, fadD).

There is also provided herein a method for producing fatty acids, said method comprising: culturing bacteria comprising at least one overexpressed acyl-ACP thioesterase gene in a growth medium in a container having walls; allowing said bacteria to secrete (or otherwise release) fatty acids; and collecting said fatty acids. Collecting said fatty acids can comprise decanting said bacteria and said growth medium; and collecting said fatty acids by hydrophobic solvent extraction from the walls of said container. Alternatively, fatty acids can be collected by collecting a solid fraction of said fatty acids by filtration of said medium. Collecting said fatty acids can also comprise collecting a solid fraction of said fatty acids by filtration of said medium; and extracting the remaining solids from the walls of said container with a hydrophobic solvent. Alternatively, collecting said fatty acids can comprises rinsing said walls with an alkali solution, and/or evaporating said hydrophobic solvent.

In yet other embodiments, the growth medium can be supplemented with an acid, for example acetic acid or HCL to increase fatty acid production.

DESCRIPTION OF EMBODIMENTS OF THE INVENTION

Figure 1:
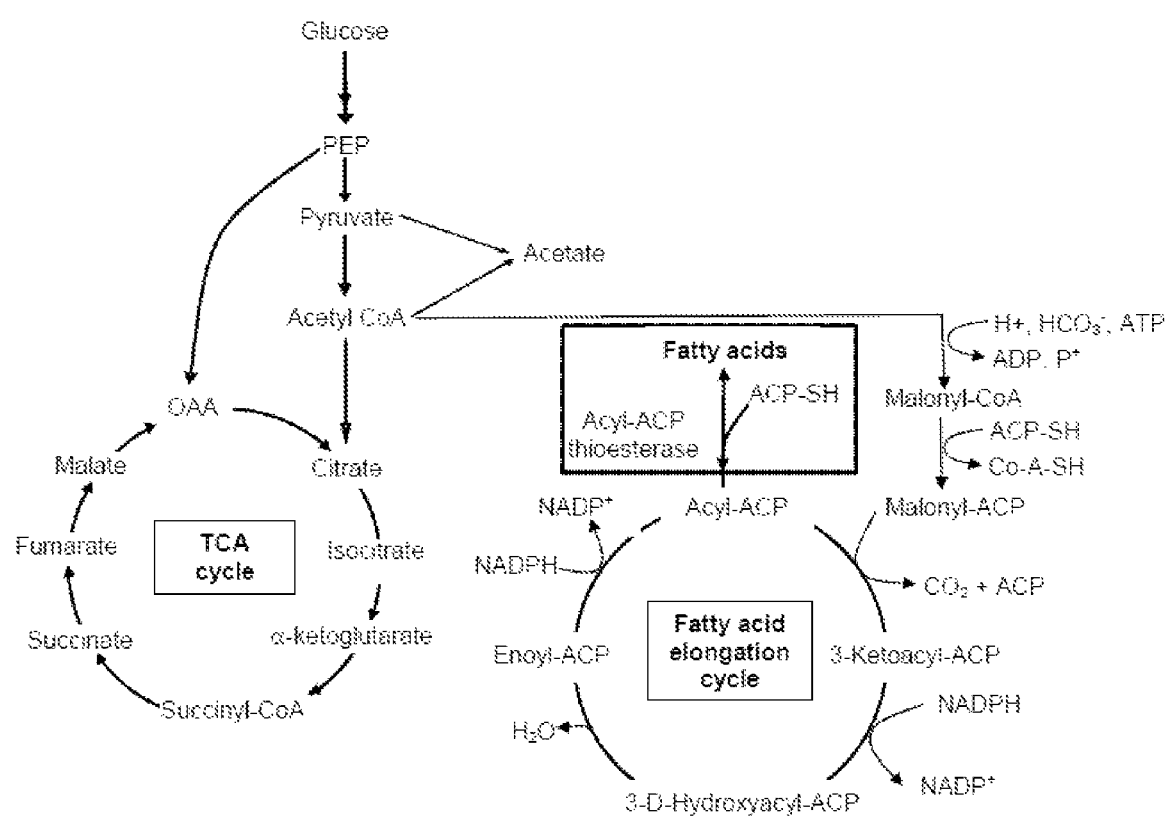
FIG. 1. Simplified central aerobic metabolic pathway of *E. coli* including the newly added free fatty acid production pathway.

The following abbreviations are used herein:

| | |
|---|---|
| ACC | Acetyl-CoA carboxylase |
| acc | Gene encoding Acetyl-CoA carboxylase |
| ACP or acyl-ACP | Acyl-acyl carrier protein |
| FA | Fatty acid |
| fabD | Gene encoding malonyl CoA-acyl carrier protein transacylase |
| fadD | Gene encoding fatty acyl-CoA synthetase |
| FID | Flame ionization detector |
| fumAC | Gene encoding bnoth fumarase A, fumarase C |
| gapA | Gene encoding a component of glyceraldehyde 3-phosphate dehydrogenase-A complex |
| GC/MS | Gas chromatography mass spectroscopy |
| glk | Gene encoding glucokinase |
| gltA | Gene encoding citrate synthase |
| HPLC | High performance liquid chromatography |
| IPTG | Isopropyl β-D-1-thiogalactopyranoside |
| LB | Luria-Bertoni |
| NADPH | Nicotinamide adenosine dinucleotide phosphate hydride |
| NADK | NAD Kinase |
| pfkA | Gene encoding 6-phosphofructokinase-1 |
| ptsG | Gene encoding glucose phosphotransferase enzyme IIBC aka glucose permease |
| pykF | Gene encoding a component of pyruvate kinase I |
| sucC | Gene encoding succinyl-CoA synthetase beta subunit |
| TE | Thioesterase |
| TE$_{Rc}$ | Thioesterase from *Ricinus communis* |
| TIC | Total ion chromatogram |

The use of the word "a" or "an" when used in conjunction with the term "comprising" in the claims or the specification means one or more than one, unless the context dictates otherwise.

The term "about" means the stated value plus or minus the margin of error of measurement or plus or minus 10% if no method of measurement is indicated.

The use of the term "or" in the claims is used to mean "and/or" unless explicitly indicated to refer to alternatives only or if the alternatives are mutually exclusive.

The terms "comprise", "have", "include" and "contain" (and their variants) are open-ended linking verbs and allow the addition of other elements when used in a claim.

As used herein, the expressions "microorganism," "bacteria", "strain" and the like may be used interchangeably and all such designations include progeny. It is also understood that all progeny may not be precisely identical in DNA content, due to deliberate or inadvertent mutations. Mutant progeny that have the same function or biological activity as screened for in the originally transformed cell are included. Where distinct designations are intended, it will be clear from the context.

Reference to proteins herein can be understood to include reference to the gene encoding such protein. Thus, a claimed "permease" protein can include the related gene encoding that permease. However, it is preferred herein to refer to the protein by name, since the gene names in bacteria are largely meaningless and vary widely between species (e.g., the glucose permease gene in *E. coli* is ptsG).

"Operably associated" or "operably linked", as used herein, refer to functionally coupled nucleic acid or amino acid sequences.

"Recombinant" is relating to, derived from, or containing genetically engineered material. In other words, the genome was intentionally manipulated in some way.

"Reduced activity" or "inactivation" is defined herein to be at least a 75% reduction in protein activity, as compared with an appropriate control species. Preferably, at least 80, 85, 90, 95% reduction in activity is attained, and in the most preferred embodiment, the activity is eliminated (100%). Proteins can be inactivated with inhibitors, by mutation, or by suppression of expression or translation, by knock-out, by adding stop codons, by frame shift mutation, and the like. By "null mutant" or "null mutation" what is meant is that the mutation produces undetectable active protein. A gene can be completely (100%) reduced by knockout or removal of part of all of the gene sequence. Use of a frame shift mutation, early stop codon, point mutations of critical residues, or deletions or insertions, and the like, can also completely inactivate (100%) gene product by completely preventing transcription and/or translation of active protein. All null mutants herein are signified by Δ.

"Overexpression" or "overexpressed" is defined herein to be at least 150% of protein activity as compared with an appropriate control species. Preferably, the activity is increased 100-500%. Overexpression can be achieved by mutating the protein to produce a more active form or a form that is resistant to inhibition, by removing inhibitors, or adding activators, and the like. Overexpression can also be achieved by removing repressors, adding multiple copies of the gene to the cell, or up-regulating the endogenous gene, and the like. All overexpressed genes or proteins are signified herein by "+".

Acyl-acyl carrier protein (ACP) thioesterase is an enzyme that terminates the intraplastidial fatty acid synthesis in plants by hydrolyzing the acyl-ACP intermediates and releasing free fatty acids to be incorporated into glycerolipids. These enzymes are classified in two families, FatA and FatB, which differ in amino acid sequence and substrate specificity. Generally speaking, the N terminal (aa 1-98) of any acyl-ACP thioesterases controls the substrate specificity of the enzyme, and it is known how to change substrate specificity by swapping amino terminal domains.

Many acyl-ACP thioesterase proteins are known and can be added to bacteria for use in the invention (e.g., CAA52070, YP_003274948, ACY23055, AAB71729, BAB33929, to name a few of the thousands of such proteins available), although we have used plasmids encoded plant genes herein. Such genes can be added by plasmid or other vector, or can be cloned directly into the genome. In certain species it may also be possible to genetically engineer the endogenous protein to by overexpressed by changing the regulatory sequences or removing repressors. However, overexpressing the gene by inclusion on selectable plasmids that exist in hundreds of copies in the cell may be preferred due to its simplicity, although permanent modifications to the genome may be preferred in the long term for stability reasons.

EXAMPLE 1

Culture Growth Conditions

Unless otherwise noted, the strains were grown in 250-mL flasks with 40 mL Luria-Bertani (LB) broth or Super Broth (SB) medium supplemented with about 15 g/L glucose, 1 mM isopropyl β-D-1-thiogalactopyranoside (IPTG), and an appropriate amount of ampicillin. The cultures were grown in a rotary shaker at 250 rpm. Samples of media were taken at 24 and 48 hours after inoculation. The data shown are means for triplicate experiments at the desired time points.

EXAMPLE 2

Engineered Bacterium for Producing Fatty Acid

A novel approach was developed to increase the production of free fatty acids by deactivating one or more of the TCA cycle gene(s) (thus reducing competitive pathways) and adding a fatty acid synthesis pathway. As an example, the deactivation of the sucC gene, which encodes the succinyl-CoA synthetase beta subunit, results in about a 50% increase in fatty acid production.

FIG. 1 shows a simplified central aerobic metabolic pathway of *Escherichia coli* using glucose, for example, as a carbon source. Also included in FIG. 1 are the fatty acid biosynthesis pathways. Note that each fatty acid elongation cycle increases the carbon chain length of the fatty acids by two. Free fatty acids can be produced by introducing a fatty acyl-thioesterase gene (see FIG. 1, central dotted box). The presence of the thioesterase breaks the fatty acid elongation cycle and releases free fatty acids (Davis et al., 1993; Lu et al., 2008).

Two strains, ML 103 (a fadD mutant strain) and ML 163 (a fadD, sucC double mutant strain), were used in this example. Both strains carried a plasmid carrying a heterologous acyl-ACP thioesterase gene. The overexpression of an acyl-ACP thioesterase gene lead to the production free fatty acids (FIG. 1).

We used the fadD mutant strain as a base strain because it is often used in the literature and easily available. However, the fadD mutant is optional to the invention. In fact, we have shown that the strain ML103 (a fadD knockout mutant strain) and its parent strain MG1655 (lacking the fadD knockout) both accumulated similar quantities of free fatty acid when both with overexpressed acyl-ACP thioesterase (data not shown).

Various experiments were performed with varied sampling time and substrate concentration to test the feasibility of the system. The fatty acids ("FA") were analyzed and quantified by GC/MS and GC/FID after sonication, extraction and derivatization. Odd number saturated straight chain fatty acids, such as $C_{13}$, $C_{15}$ and/or $C_{17}$, were used as the internal standard. The results are shown in the table below:

| Strain | Free FA (g/l) | % improvement | Yield (g FA/g glucose) | % improvement |
|---|---|---|---|---|
| 24 hrs | | | | |
| Control: ML103 (ΔfadD acyl-ACP thioesterase+) | 1.34 | | 0.123 | |
| ML163 (ΔfadD, ΔsucC acyl-ACP thioesterase+) | 2.00 | 49 | 0.150 | 22 |
| 48 hr | | | | |
| Control: ML103 (ΔfadD acyl-ACP thioesterase+) | 2.20 | | 0.122 | |
| ML163 (ΔfadD, ΔsucC acyl-ACP thioesterase+) | 3.42 | 56 | 0.150 | 23 |

These results indicate the TCA cycle disrupted strain accumulated more fatty acids than that of the control strain, thus indicating that combining a thioesterase gene with a disruption in one of the genes of the TCA cycle further improves fatty acid production. The metabolite concentrations from the 24 and 48 hr samples were also analyzed using standard HPLC methodology. Acetate was observed to be the major by product (not shown).

The glucose yield (expressed in grams of total fatty acids formed per grams of glucose consumed) for the TCA cycle disrupted strain (ΔsucC) was 0.15, which is more than 22% higher than that of the control strain. A glucose yield of at least 0.19 was obtained at 24 hrs when 15 g of glucose was used (data not shown).

Figure 2:
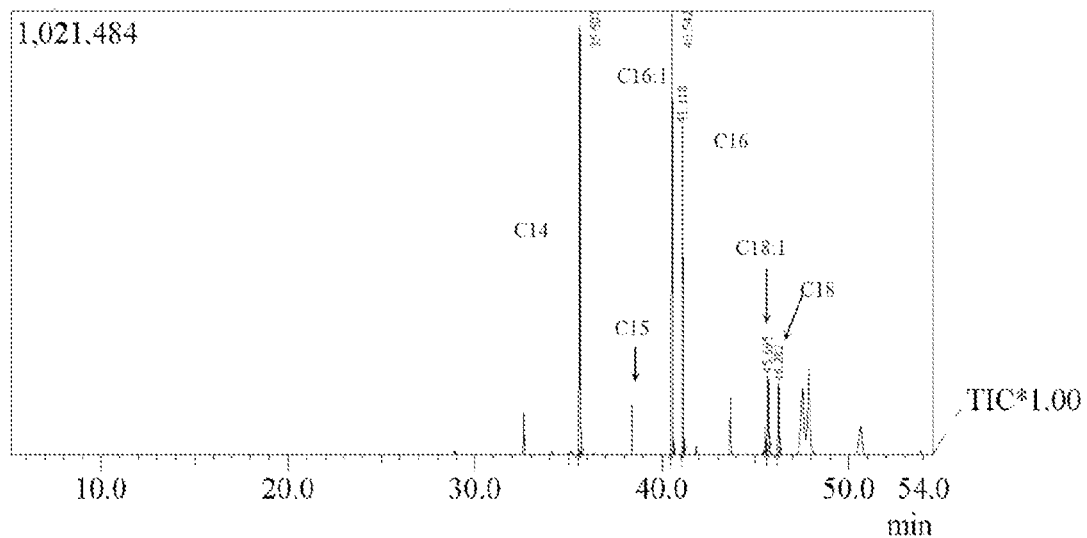
FIG. 2. A typical GC/MS total ion chromatogram (TIC) trace of the methyl ester derivatives of fatty acids. The peaks for $C_{14}$, $C_{15}$, $C_{16:1}$, $C_{16}$, and $C_{18:1}$ fatty acids are labeled.
Figure 3:
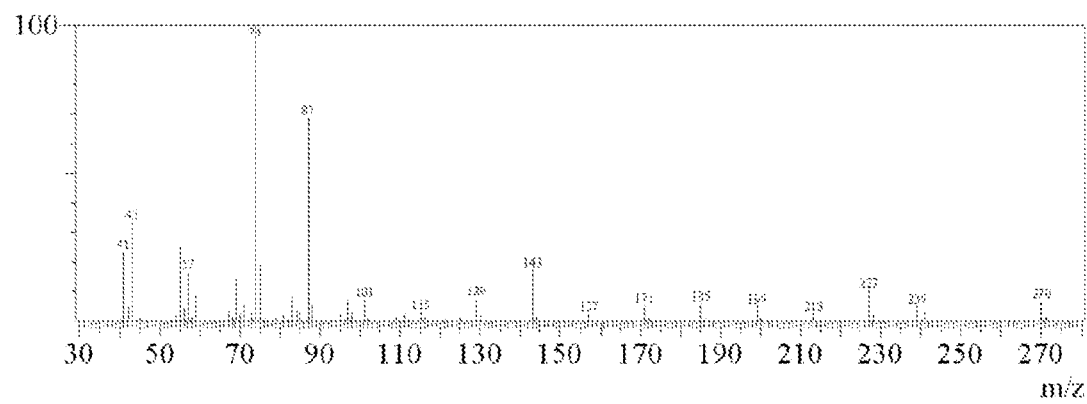
FIG. 3. Mass spectrum of a $C_{14}$ saturated straight chain fatty acid. Total run time as 35.6 minutes.

The methyl esters of the fatty acids were analyzed by GC/MS and GC/FID. A typical GC/MS total ion chromatogram (TIC) trace of the methyl ester derivatives of fatty acids is shown in FIG. 2. Peak assignment is based on the corresponding mass spectrum (mass spectrum library created from authentic standards, commercial library and/or literature). The mass spectrum of $C_{14}$ saturated straight chain fatty acids is also included in FIG. 3, as an example. Most data of this nature has been omitted herein, but is available on request.

In addition to the ΔsucC mutation described above, we tested a couple of other genes in the TCA cycle to determine if it was a generally applicable phenomena that reducing or deleting such genes improves fatty acid production. Thus, in the experiment below, we tested ΔfumAC (fumarase A and fumarase C), and ΔgltA (citrate synthase). These mutations did allow increased fatty acid production per mole of glucose, but the ΔsucC mutant (above) was still the best performer.

| Strain | Fatty acid (g/l) | % change | Yield (g fatty acid/g glucose used) | % change |
|---|---|---|---|---|
| | | 24 hrs | | |
| ML103(pXZ18) | 1.70 | | 0.154 | |
| MLK193(pXZ18) | 1.57 | −8 | 0.178 | 16 |
| MLK195(pXZ18) | 1.15 | −32 | 0.180 | 17 |
| | | 48 hrs | | |
| ML103(pXZ18) | 2.60 | | 0.131 | |
| MLK183(pXZ18) | 2.68 | 3 | 0.149 | 14 |
| MLK195(pXZ18) | 2.48 | −5 | 0.136 | 4 |

ML103(pXZ18) = control with + TE$_{Rc}$
MLK193(pXZ18) = ML103, ΔfadD, ΔfumAC + TE$_{Rc}$
MLK195(pXZ18) = ML103, ΔfadD, ΔgltA + TE$_{Rc}$ Both mutant strains give similar total fatty acids at 48 hrs, but with higher yields.

EXAMPLE 3

Additional Engineering

Since it appears to be a general phenomena that adding a thioesterase gene, coupled with TCA cycle reductions or deletions improves fatty acid production, we also tested a variety of other mutations and discovered some additional general principals: 1) Glycolysis gene disruption can also improve fatty acid production. 2) Combined glycolysis and TCA cycle gene disruption can further improve fatty acid production. 3) Overexpression of coenzyme A-acyl carrier protein transacylase (fabD) can increase free fatty acid production. 4) Moderate overepression of acetyl-CoA carboxylase (acc) can increase free fatty acid production. However, there is an optimal level overexpression, and too high an expression may result in minimal improvement.

Glycolysis gene manipulation: We tested a few glycolytic mutants to determine if reducing or deleting glycolytic enzymes would shift carbons towards fatty acid production, and were able to confirm that perturbing glycolysis resulted in significant improvement in fatty acid production. All glycolysis mutant strains give better yields at 24 and 48 hours. The Δglk and ΔpykF also resulted in higher total fatty acid production.

| Strain | Fatty acid (g/l) | % change | Yield (g fatty acid/g glucose used) | % change |
|---|---|---|---|---|
| | | 24 hrs | | |
| ML103(pXZ18) | 1.58 | | 0.160 | |
| MLK189(pXZ18) | 1.64 | 4 | 0.250 | 56 |
| MLK190(pXZ18) | 1.28 | −19 | 0.261 | 63 |
| MLK191(pXZ18) | 1.16 | −27 | 0.234 | 47 |
| MLK192(pXZ18) | 1.66 | 5 | 0.219 | 37 |
| | | 48 hrs | | |
| ML103(pXZ18) | 3.09 | | 0.168 | |
| MLK189(pXZ18) | 3.43 | 11 | 0.212 | 26 |
| MLK190(pXZ18) | 2.60 | −16 | 0.235 | 40 |
| MLK191(pXZ18) | 2.53 | −18 | 0.205 | 22 |
| MLK192(pXZ18) | 3.36 | 9 | 0.207 | 23 |

MLK189(pXZ18) = ML103, ΔfadD, Δglk + TE$_{Rc}$
MLK190(pXZ18) = ML103, ΔfadD, ΔptsG + TE$_{Rc}$
MLK191(pXZ18) = ML103, ΔfadD, ΔpfkA + TE$_{Rc}$
MLK192(pXZ18) = ML103, ΔfadD, ΔpykF + TE$_{Rc}$
fadD = dodecenoyl-CoA δ-isomerase, aka enoyl-CoA hydratase, 3-hydroxybutyryl-CoA epimerase, 3-hydroxyacyl-CoA dehydrogenase (a component of the fatty acid oxidation complex)
glk = glucokinase
ptsG = glucose phophotransferase enzyme IIBC aka glucose permease
pfkA = 6-phosphofructokinase-1
pykF = Component of pyruvate kinase I Combined glycolysis and TCA cycle gene manipulation. We next sought to determine if perturbations in both the TCA cycle and glycolysis would have an additive effect by combining a TCA cycle mutant (sucC) with the best of the glycolytic mutants Δglk and ΔpstG.

| Strain | Fatty acid (g/l) | % change | Yield (g fatty acid/g glucose used) | % change |
|---|---|---|---|---|
| | | 24 hrs | | |
| ML103(pXZ18) | 1.58 | | 0.160 | |
| MLK181(pXZ18) | 2.32 | 47 | 0.193 | 21 |
| MLK194(pXZ18) | 1.09 | −31 | 0.316 | 98 |
| | | 48 hrs | | |
| ML103(pXZ18) | 3.09 | | 0.168 | |
| MLK181(pXZ18) | 4.24 | 37 | 0.197 | 17 |
| MLK194(pXZ18) | 2.17 | −30 | 0.234 | 39 |

ML103(pXZ18) = ML103 + TE$_{Rc}$
MLK181(pXZ18) = ML103, ΔfadD, ΔsucC, Δglk + TE$_{Rc}$
MLK194(pXZ18) = ΔfadD, ΔsucC, ΔptsG + TE$_{Rc}$ Both combined glycolysis and TCA cycle mutant strains give better yields at 24 and 48 hours. The ΔsucCΔglk double mutant strain also resulted in higher fatty acid production, giving 37% increase in total free fatty acid production and 17% improvement in yield over TE alone background.

SucC mutant and sucC-glk double mutant. In order to obtain a more direct comparison of TCA versus TCA plus glycolytic mutations (with overexpressed TE from *Ricinus communis*=TE$_{Rc}$), the ΔsucC was compared directly against the ΔsucCΔglk double mutant. The data shown are means+/− standard deviation for experiments at 48 hrs (n>3). The ΔsucC and ΔsucC-Δglk double mutants produce a large quantity of free fatty acid (more than 9 g/l) with good yields (more than 0.18 g/g). The ΔsucC-Δglk double mutants, however, give a better yield than the sucC mutant alone. Therefore, it is proven that combining TCA and glycolytic mutants further improves both production and yield.

| Strain | Genotype | Fatty acid (g/l) | Yield (g FA/g Glu) |
|---|---|---|---|
| ML163(pXZ18) | ML103, ΔfadD, ΔsucC + TE$_{Rc}$ | 9.12 | 0.182 |
| MLK181(pXZ18) | ML103, ΔfadD, ΔsucC, Δglk + TE$_{Rc}$ | 10.00 | 0.199 |

FabD overexpression. Malonyl coenzyme A-acyl carrier protein transacylase (fabD) overexpression was also tested using the fabD gene from various sources. This protein was generally found to increase fatty acid production. The overexpression of fabD from *streptomycin avermitilis* and *streptomycin coelicolar* increases the fatty acid accumulation by about 20% while overexpression of fabD from *E. coli* MG1655 resulted in about an 11% increase.

| | 24 hrs | | | | |
|---|---|---|---|---|---|
| | control | aveFabD | 1655FabD | coeFabD | 824FabD |
| Total free fatty acid (g/l) | 1.1755 | 1.4168 | 1.3131 | 1.4079 | 1.1533 |
| standard deviation | 0.0160 | 0.0829 | 0.0704 | 0.0663 | 0.0647 |
| T-Test | | 1.27E−05 | 4.16E−04 | 9.40E−06 | 6.17E−01 |
| % improvement* | | 20.5294 | 11.7056 | 19.7745 | −1.8860 |

Control: carrying a plant thioesterase (TE) gene
aveFabD: carrying a plant thioesterase gene and a fabD gene from *streptomycin avermitilis*
1655FabD: carrying a plant thioesterase gene and a fabD gene from *E. coli* MG1655
coeFabD: carrying a plant thioesterase gene and a fabD gene from *streptomycin coelicolar*
824FabD: carrying a plant thioesterase gene and a fabD gene from *Clostridium acetobutylicum* ATCC 824
*% improvement based on the control strain We also tested another TE (target/leading sequence from *R. communis* and remainder from *Cuphea palustris*) to produce shorter chain fatty acids. This TE when combined with both the glycolysis mutants (ΔptsG or ΔpfkA) or a glycolysis and TCA double mutant (ΔsucC, ΔptsG) significantly improves the production of C-8 fatty acid. The mutant strains produced significantly higher fatty acids, higher than 1 g/l at 48 hrs. In addition, the fatty acid mainly consists of C-8 straight chain saturated fatty acid (>95%) (data not shown).

| Strain | Genotype | fatty acid produced (g/l) | % improvement | yield (g/g) | % improvement |
|---|---|---|---|---|---|
| | | 24 hrs | | | |
| ML103(pXZCP88) | ML103 + hybrid TE | 0.07 | | 0.039 | |
| MLK190(pXZCP88) | ML103, ΔfadD, ΔptsG + hybrid TE | 0.69 | 857 | 0.206 | 422 |
| MLK191(pXZCP88) | ML103, ΔfadD, ΔpfkA + hybrid TE | 0.63 | 766 | 0.175 | 344 |
| MLK194(pXZCP88) | ML103, ΔfadD, ΔsucC, ΔptsG + hybrid TE | 0.68 | 834 | 0.251 | 536 |
| | | 48 hrs | | | |
| ML103(pXZCP88) | ML103, ΔfadD + hybrid TE | 0.07 | | 0.014 | |
| MLK190(pXZCP88) | ML103, ΔfadD, ΔptsG + hybrid TE | 1.23 | 1718 | 0.121 | 788 |
| MLK191(pXZCP88) | ML103, ΔfadD, ΔpfkA + hybrid TE | 1.28 | 1801 | 0.110 | 710 |
| MLK194(pXZCP88) | ML103, ΔfadD, ΔsucC, ΔptsG + hybrid TE | 0.88 | 1203 | 0.131 | 864 | pXZCP88 = + hybrid TE (target/leading sequence from *R. communis* and remainder from *Cuphea palustris*.

Acetyl-coA carboxylase (ACC) overexpression. The effect of acetyl-CoA carboxylase overexpression on fatty acid accumulated was also examined. The acc subunits 2 and 3 from *Streptomyces avermitilis* were cloned under the control of a pBAD promoter system with expression level corresponding to the levels of arabinose concentration. Strain ML103 (pXZ18-1, pXZbad23) carrying two plasmids was constructed. One plasmid, pXZ18-1, contains a acyl-ACP thioesterase gene from *Ricinus Communis* and the acc subunit 1 from *S, avermitilis* (under the control of a pTrc promoter system). The other plasmid, pXZbad23, carries the acc subunits 2 and 3 from *S. avermitilis* (under the control of a pBAD promoter system).

| Arabinose concentrations (microM) | 0 | 0.005 | 0.0125 | 0.025 | 0.05 | 0.1 |
|---|---|---|---|---|---|---|
| Total free fatty acid (g/l) | 1.22 | 1.35 | 1.44 | 1.28 | 1.25 | 1.27 |
| standard deviation | 0.05 | 0.01 | 0.03 | 0.05 | 0.02 | 0.02 |
| % increase | | 10.66 | 18.27 | 5.14 | 2.24 | 3.93 |

ML103 (pXZ18-1, pXZbad23): pXZ18-1 = thioesterase gene from *R. communis* and the acc subunit 1 from *S. avermitilis*; pXZbad23 acc subunits 2 and 3 from *S. avermitilis*
* % increase based on the uninduced culture (0 arabinose)

The overexpression of ACC increases the fatty acid accumulation when compared with the control culture (uninduced culture). The effect reaches a maximum at 0.0125 μM of arabinose with an increase by about 18%. However further increase in the induction level (higher arabinose concentrations) resulted in a much less increase in the fatty acid accumulation (see table). For example, at 0.1 μM of arabinose, the total free acid is very similar to that of the control culture. These results suggest that overexpression of ACC can increase free fatty acid production. However, there is an optimal level overexpression. Too high an expression may result in minimal improvement. Therefore, by "moderate overexpression" herein, we mean that the upper level of expression should be titrate in an appropriate way, for example as described herein, and then not exceeded.

EXAMPLE 4

Method for Producing Fatty Acid

Figure 4:
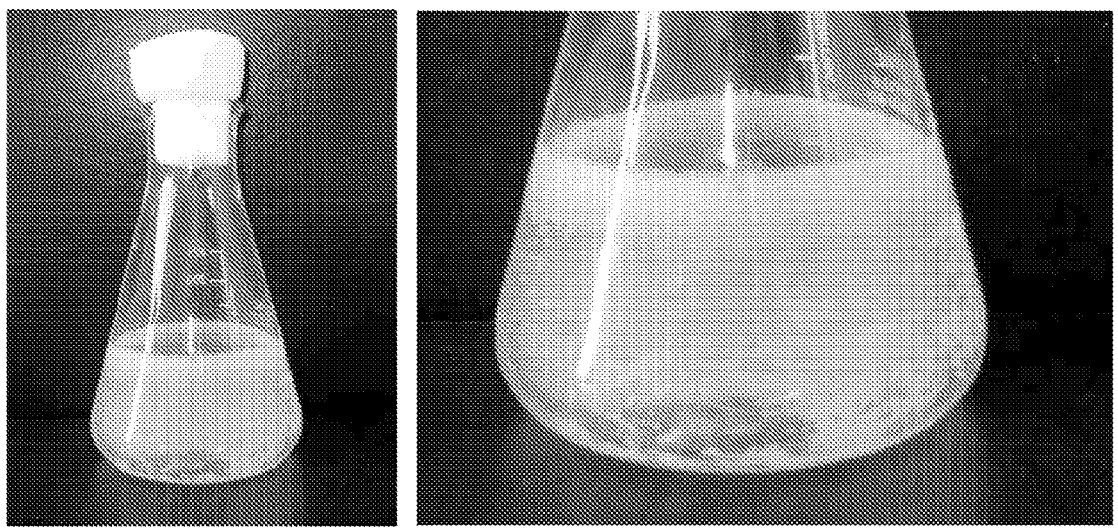
FIG. 4. Accumulation of white deposits on the side of the culture vessels or floating clumps in the fermentation broth by the engineered strains (ΔfadD, ΔsucC, TO. Samples were taken after 48 hours. This strain produced enough FA that the fats preciptated and became visible in the broth, even without added acetic acid.

In addition to the large variety of mutants and mutant combinations described above, the invention also relates to a novel process to produce free fatty acids, which when overproduced are secreted or somehow released into the medium, and appear as white deposits on the side of the culture vessels or as floating clumps in the fermentation broth (see FIG. 4). GC/MS analyses show that the deposits or clumps contain mainly free fatty acids.

The white deposits or clumps can be easily recovered by collecting solids or by extraction with a hydrophobic solvents or alkali solution. The fatty acids can be further purified using common techniques such as solvent evaporation or precipitation, and the like, if needed. Thus, the invention greatly facilitates the processing of free fatty acids from the fermentation systems by eliminating the need to disrupt the cells first. The cells can be used again to produce fatty acids, further improving the cost effectiveness. *Escherichia coli* strains that carry a plasmid containing a heterologous acyl-ACP TE gene were used in this study.

Figure 5:
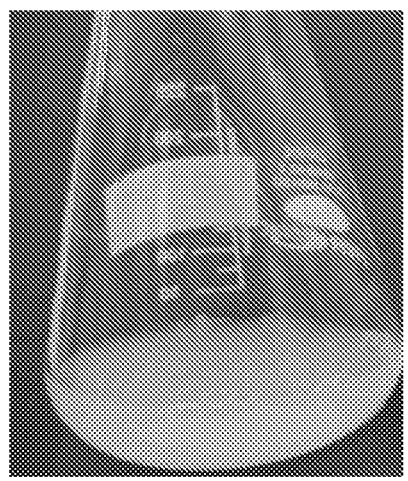
FIG. 5. The engineered cells were grown in flasks. Pictures shown were taken at 2 days hours (left picture) and 5 days (right picture) after inoculation. Less accumulation of white deposits on the side of the culture vessels by the engineered strains (ΔfadD, ΔsucC, TE+, but a different colony than used for FIG. 4 that produces less FA) is observed without added acetic acid. The fatty acid is still produced, but not precipitated and thus not visible.
Figure 5:
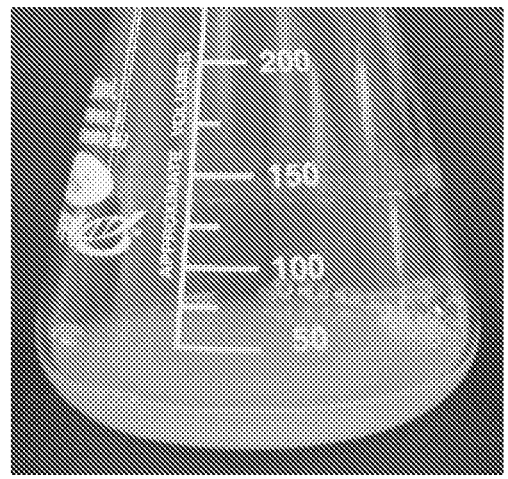
Figure 6:
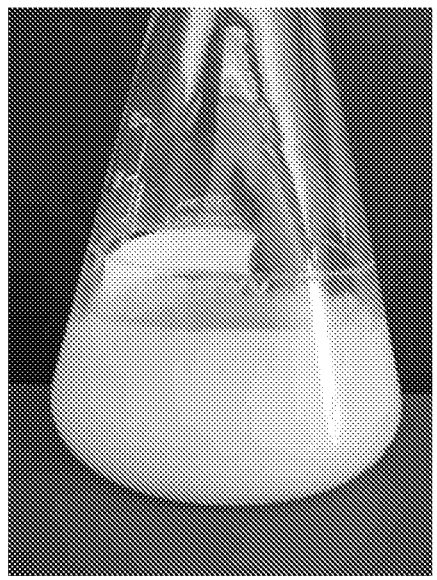
FIG. 6. Accumulation of white deposits on the side of the culture vessels by the same engineered strain of FIG. 5 (ΔfadD, ΔsucC, TE). An appropriate quantity of acetic acid was added at 24 hours after inoculation. White deposits or clumps started to appear soon after the acetic acid addition. Pictures shown were taken at 5 days after inoculation.
Figure 6:
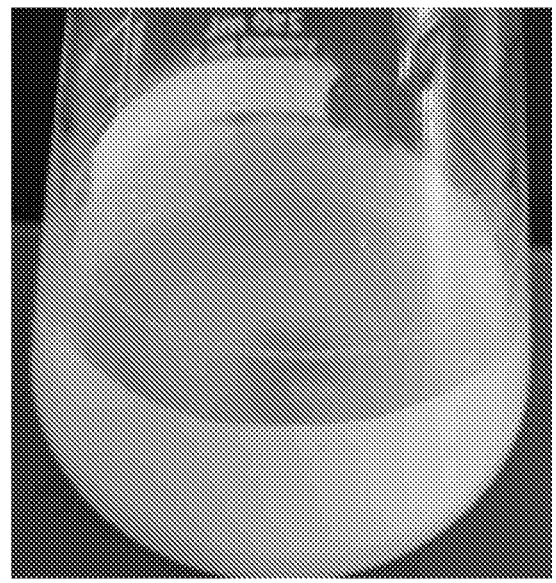

Various experiments were performed with varied sampling time and substrate concentration to test the formation of white clumps and white deposits on stimulation with acid. The results are shown in FIGS. 5-6. Little accumulation of white deposits on the side of the culture vessels by the engineered strains can be observed without added acetic acid (FIG. 5). When an appropriate quantity of acetic acid was added 24 hours after inoculation, white deposits or clumps appeared soon after addition. FIG. 6 shows these flasks 110 hours after inoculation. We have also tested HCL with similar results (data not shown). Therefore, it appears to be a general phenomenum that adding acid to cultures improves FA secretion. By "secretion" herein we do not mean to imply any particular mechanism, but only that the FA exits the cells in some wasy and accumulated in the media.

EXAMPLE 5

NADPH Availability

Another novel approach is developed to increase the production of free fatty acids by increasing NADPH availability.

The ΔfadD mutant strain was used as a background because this knockout mutation is thought to increase the amount of fatty acid produced, but it is optional. Further, although we used *E. coli* udhA gene and the castor bean acyl-ACP thioesterase gene, these genes could be from any species providing the resulting proteins have the same catalytic function. In fact, we have thioesterase genes from 4 sources that can be used interchangeably herein. Additionally, although we used *E. coli* as the bacterial cell, several different bacteria are available and already in use industrially and the cloning techniques are standard in the art and can easily be applied to any bacterium. Further, other microorganisms, such as yeast or algae can be used if engineered as described herein because the pathways involved are ubiquitous.

Figure 7:
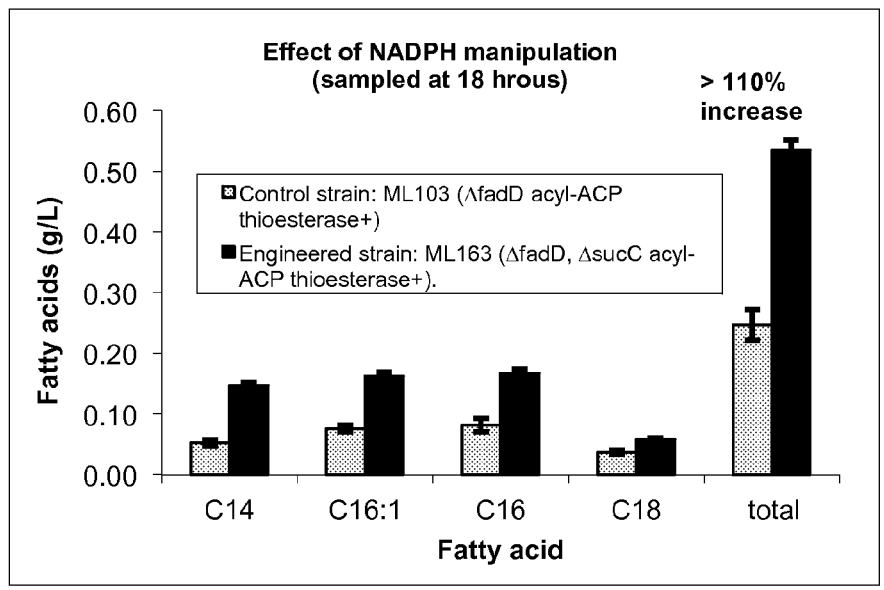
FIG. 7. Accumulation of fatty acids by the control strain and the engineered strain (18 hours after inoculation). The engineered strain produces 110% more fatty acids. Samples of the media were taken at 18 hours after inoculation. Control strain: ML103 (ΔfadD and acyl-ACP thioesterase+). Engineered strain: ML163 (ΔfadD, ΔsucC and acyl-ACP thioesterase+).
Figure 8:
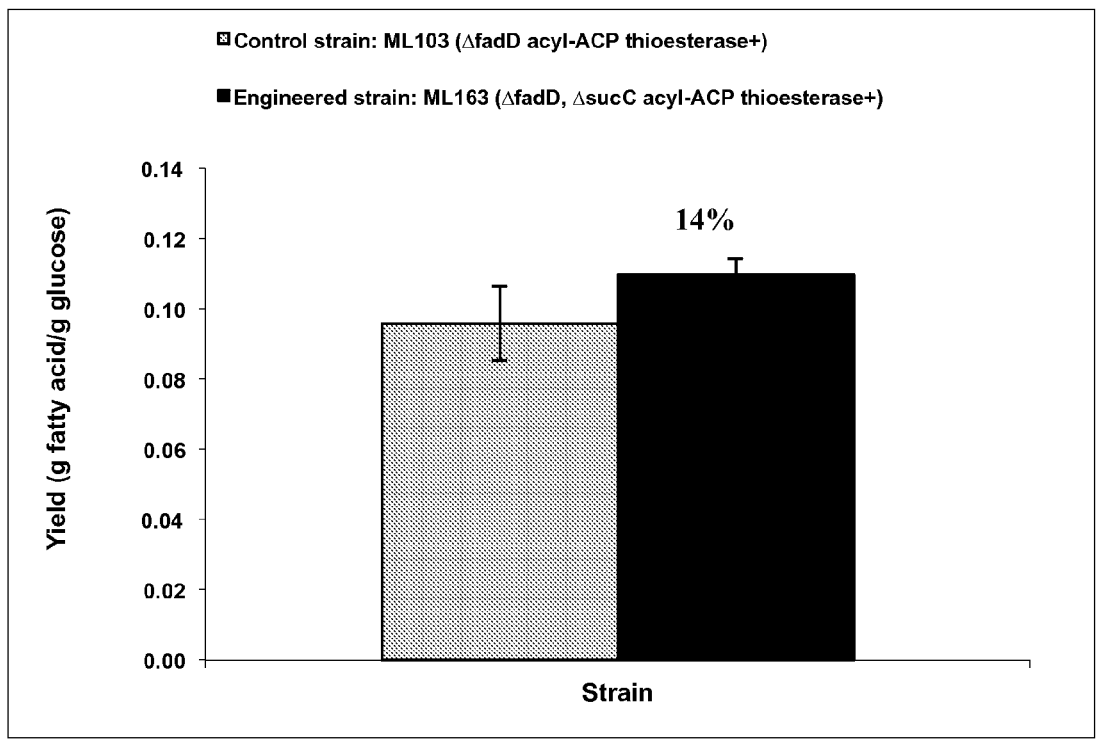
FIG. 8. Yield in grams of total fatty acids per gram of glucose at 18 hours. Control strain: ML103 (ΔfadD and acyl-ACP thioesterase+) Engineered strain: ML 163 (ΔfadD, ΔsucC and acyl-ACP thioesterase+).

Various experiments were performed with varied sampling time and substrate concentration to test the feasibility of the system. The results are shown in FIGS. 7 and 8. The fatty acids were analyzed and quantified by GC/MS and GC/FID after sonication, extraction and derivation. Odd number saturated straight chain fatty acids, such as $C_{13}$, $C_{15}$ and/or $C_{17}$, were used as the internal standard. The results shown in FIG. 7 are the sum of all major free fatty acids in the sample. FIG. 7 shows the engineered strain accumulated more fatty acids that that of the control strain (>110%).

The metabolite concentrations from the 18-hour samples were also analyzed using standard HPLC methodology. Acetate was observed to be the major byproduct. The glucose yield (expressed in grams of total fatty acids formed per gram of glucose consumed) for the engineered strain is at 0.11, which is more that 14% higher than that of the control strain (FIG. 8).

We also tested NAD-Kinase (NADK), another protein that will help to provide reducing equivalents, and it also improves production when overexpressed, either alone or with a glycolytic mutant (ΔgapA) per the following table.

| | | Fatty acids (g/l) at 18 h | | | | |
|---|---|---|---|---|---|---|
| Strain | Genotype | C14 | C16:1 | C16 | C18:1 | Total |
| ML103 (pXZ18, pDHC29) | ML103, ΔfadD + $TE_{Rc}^+$ + control vector pDHC29 | 0.02 | 0.03 | 0.04 | 0.02 | 0.11 |
| ML103 (pXZ18, pNADK) | ML103, ΔfadD + $TE_{Rc}^+$ + $NADK^+$ | 0.27 | 0.32 | 0.21 | 0.09 | 0.88 |
| MG1655A (pXZ18, pDHC29) | MG1655, ΔgapA + $TE_{Rc}^+$ + control vector pDHC29 | 0.04 | 0.05 | 0.06 | 0.03 | 0.19 |
| MG1655A (pXZ18, pNADK) | MG1655, ΔgapA + $TE_{Rc}^+$ + $NADK^+$ | 0.31 | 0.29 | 0.21 | 0.08 | 0.88 |

As an example, the overexpression of udhA, which encodes a soluble transhydrogenase UdhA, results in more than 110% increase in fatty acid production. Two strains ML103 (a ΔfadD mutant strain) carrying either a control vector or a vector containing the udhA gene were described in Sanchez et al. (2006). Both strains are engineered to also carry a plasmid carrying a heterologous acyl-ACP thioesterase gene.

EXAMPLE 6

Summary of Plant-Derived Thioesterases

Another development in the area of fatty acid synthesis was to test the efficacy of various acyl-ACP thioesterases, combinations thereof, and methods of preferentially making short or long chain fatty acids. Host bacterial strains ML103 (a fadD mutant strain) or K27 (another fadD mutant strain) carrying plasmids that contain different acyl-ACP thioesterases were used in this study. Various experiments were performed to test the free fatty acid synthesizing capability of the various acyl-ACP thioesterases. Our main observations were:

1) Overexpression of acyl-ACP thioesterases *Ricinus communis* and *Jatropha curcas* enables the production of large quantities of free fatty acids.

2) The leading (targeting) sequence from some plant thioesterases, such as *Ricinus communis* or similar sequences, can be used to construct hybrid acyl-ACP thioesterases which allow a significant increase in free fatty acid production, including short chain free fatty acids.

3) The leading (targeting) and/or the C-terminal end sequence from some plant thioesterases, such as *Ricinus communis* or similar sequences, can be used to construct hybrid acyl-ACP thioesterases that allow a significant increase in free fatty acids production. Thus, increases can be achieved with terminal sequence similar to that of *Ricinus communis*, and the remainder selected from a TE having the required specificity.

By "remainder" herein it will be apparent that the reader is to obtain the remaining sequences from another TE. Thus, if aa 1-40 are from one species, aa 41-end is the remainder. In the alternative, the leader sequence can be excluded entirely, so that aa 81-end are used instead (assuming the leader is aa 1-80). Similarly, if aa 397-end are from one species, aa 1-396 is the remainder or aa 81-396 if the leader is omitted.

Figure 9:
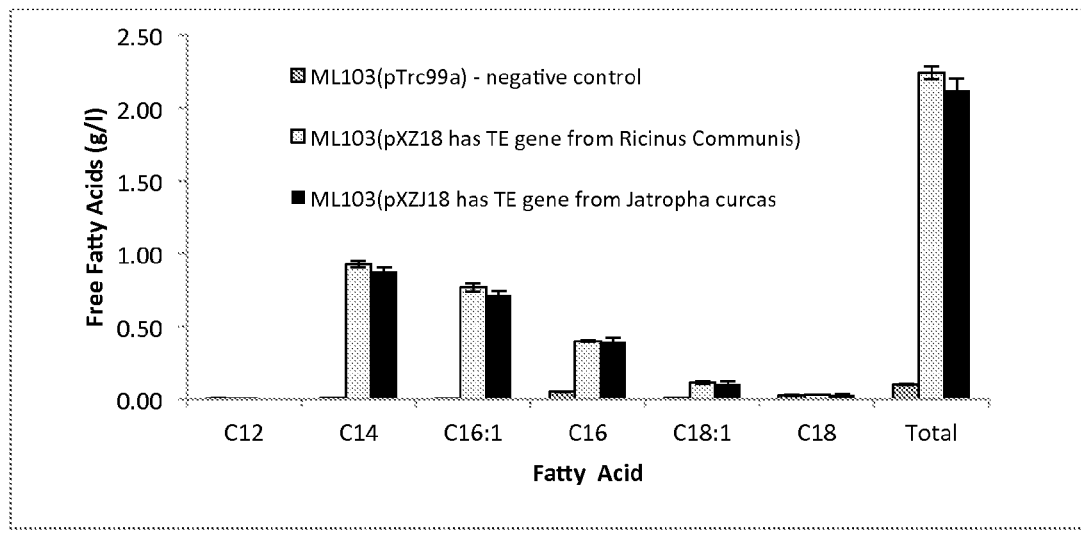
FIG. 9. Accumulation of fatty acids by the control strain and the engineered strains. The engineered strains produced more than 2.0 g/L of free fatty acids while the control strain only produced approximately 0.1 g/L. Samples of the media were taken at 48 hours after inoculation. ML103(pTrc99a) is the negative control. ML103(pXZ18) has the TE gene from *Ricinus communis*. ML103(pXZJ18) has the TE gene from *Jatropha curcas*.
Figure 10:
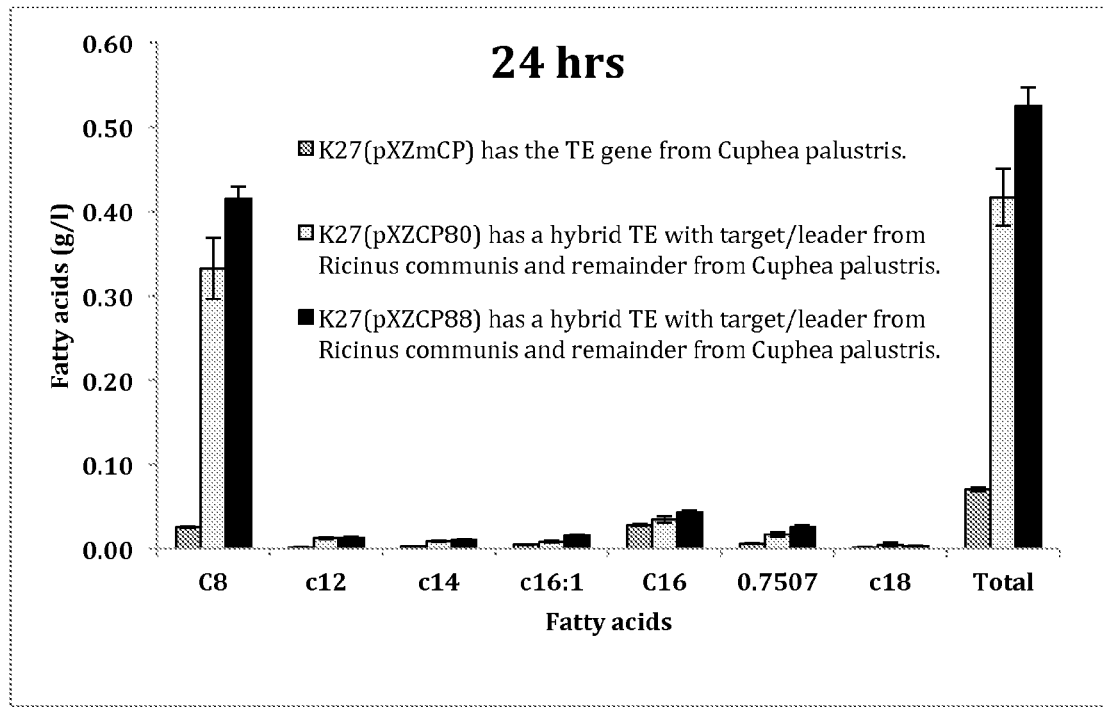
FIG. 10. Accumulation of fatty acids by strains containing plasmids that carrying either an acyl-ACP thioesterases from *Cuphea palustris* or the hybrid acyl-ACP thioesterases. Samples of the media were taken at 24 after inoculation.

TE from *Ricinus communis* and *Jatropha curcas*: Shake flask experiments were carried out with three genetically engineered strains with ML103 as the host. The plasmid ptrc99a was used as the cloning vector. The expression of the acyl-ACP thioesterase was put under the control of a tac promoter system. The three strains are the host strain ML103 carrying plasmid pTrc99a serving as the control, plasmid pXZ18 containing a TE gene from *Ricinus communis* and plasmid pXZJ18 containing a TE gene from *Jatropha curcas*, respectively. The results shown in FIG. 9 are the compositions and the sum of all major free fatty acids in the samples at 48 hours, clearly showing that the strain carrying the thioesterases from *Ricinus communis* or *Jatropha curcas* accumulated much more fatty acids than that of the control strain (>2 g/L vs. 0.1 g/L).

TE Domains from *Ricinus communis*: Shake flask experiments were carried out with two genetically engineered strains with ML103 as the host. The plasmid ptrc99a was used as the cloning vector. The expression of the acyl-ACP thioesterase was put under the control of a tac promoter system. The two strains are the host strain ML103 carrying plasmid pXZ18 containing a TE gene from *Ricinus communis*, including its leading/targeting sequence, and plasmid pXZm18 containing a TE gene from *Ricinus communis* without its leading/targeting sequence. The results shown in the table below are the compositions and the sum of all major free fatty acids in the samples at 48 hours, clearly showing that the strain carrying the thioesterase from *Ricinus communis* ($TE_{Rc}$) with the leading/targeting sequence accumulated about 10-fold more fatty acid than that of the strain carrying the same thioesterase from *Ricinus communis* without the leading/targeting sequence (>2 g/L vs. ~0.2 g/L). Thus, this experiment shows that the leader sequence of $TE_{Rc}$ has a profound effect on fatty acid synthesis. It is noted herein that in the native species, the leader is normally cleaved off, yet when retained in bacteria (which presumably lack the enzymes to cleave the leader), production is significantly increased. Thus, the full length protein is more active than the shorter mature protein!

| Strain | Free fatty acid (g/l) | | | | | | |
|---|---|---|---|---|---|---|---|
| | C12 | C14 | C16:1 | C16 | C18:1 | C18 | Total |
| ML103 (pXZm18) | 0.0015 | 0.0310 | 0.0183 | 0.1370 | 0.0240 | 0.0116 | 0.2233 |
| ML103 (pXZ18) | 0.0055 | 0.9265 | 0.7675 | 0.3986 | 0.1145 | 0.0299 | 2.2424 |

ML103 (pXZm18): has the TE gene from *Ricinus communis* without the leading/targeting sequence
ML103 (pXZ18): has the TE gene from *Ricinus communis*

Hybrid TE: The leading/targeting sequence from *Ricinus communis* was then used to increase free fatty acid production by constructing a hybrid acyl-ACP thioesterase from *Diploknema butyracea*. The resulting amino acid sequence of the hybrid Acyl-ACP thioesterase is shown below with the added sequence from *Ricinus communis* underlined. The results shown in the table below are the compositions and the sum of all major free fatty acids in the samples at 48 hours, clearly showing that the strain carrying the hybrid acyl-ACP thioesterase accumulated about 16-fold more fatty acid than that of the strain carrying the same acyl-ACP thioesterase without the leading sequence from *Ricinus communis* (>2.2 g/L vs. ~0.13 g/L). Below is the specific thioesterase sequences studied.

| Strain | Free fatty acid (g/l) | | | | | | |
|---|---|---|---|---|---|---|---|
| | C12 | C14 | C16:1 | C16 | C18:1 | C18 | Total |
| ML103 (pXZ16) | 0.0086 | 0.0078 | 0.0066 | 0.0573 | 0.0094 | 0.0434 | 0.1331 |
| ML103 (pXZr16) | 0.0044 | 0.9353 | 0.7291 | 0.4280 | 0.1435 | 0.0204 | 2.2607 |

ML103 (pXZ16): has the TE gene from *Diploknema butyracea*.
ML103 (pXZr16): has a hybrid acyl-ACP thioesterase with leading/targeting sequence from *Ricinus communis* and remainder of gene from *Diploknema butyracea* pXZr16: hybrid acyl-ACP thioesterase with leading/targeting sequence from *Ricinus communis* and remainder of gene from *Diploknema butyracea*. The leading/targeting sequence from *Ricinus communis* underlined (SEQ ID NO. 1):

<u>MVATAAAATSSFFPVPSQSADANFDKAPASLGGIKLKSTSCSRGLQVKAN</u>

<u>AQAPPKINGSSVGFTTSVETVKNDGDMPLPPPP</u>RTMINQLPDWSMLLAAI

TTIFLAAEKQWMMLDWKPRRPDMIIDSFGLGKIVQDGLVFRQNFSIRSYE

IGADRTASVETMMNHLQETALNHVRAAGLMADGFGATPEMSKRNLIWVVT

KMQVLVDRYPKWGDVVQVETWIAAYGKNCMRRDWFVRDCKTGDIITRASS

VWVMMNKETRRLSKIPHEVRCEIGSYFVDSPPVLAEDSRKLRKLDESTAD

YICTGLKPRWSDLDVNQHVNNVKYIGWILETAPQLILESHELCGMTLEYR

RECGKDSVLQSMTAVSGGAIGGLVDPGYVECQHLLRLEDGAEIVKARTHW

RPKYANCLGSHGQLPAESA

Hybrid TE for making short fatty acids: The leading/targeting sequence from *Ricinus communis* was used to increase short chain free fatty acid production by constructing two hybrid acyl-ACP thioesterases from *Cuphea palustris*. The resulting amino acid sequences of the two hybrid Acyl-ACP thioesterases, XZCP80 and XZCP88, are shown below with the sequence from *Ricinus communis* underlined. The compositions and the sum of all major free fatty acids in samples taken at 24 and 48 hours are not shown herein, but clearly indicate that both strains carrying the hybrid acyl-ACP thioesterases accumulated significantly more free fatty acids than that of the control strain carrying the same acyl-ACP thioesterase without the leading sequence from *Ricinus communis*. In addition, both hybrid acyl-ACP thioesterases XZCP80 and XZCP88 produce $C_8$ free fatty acid (>0.3 g/L) as the major product. The percentage of $C_8$ is more than 79% at 24 hours for both strains carrying the hybrid acyl-ACP thioesterases. Note that the control strain with the mature *Cuphea palustris* acyl-ACP thioesterases only produced less than 0.03 g/L of $C_8$ free fatty acids. Below are the specific transferases studied.

XZCP80: Amino acid sequence of a hybrid acyl-ACP thioesterases with the leading/targeting sequence from *Ricinus communis* underlined (SEQ ID NO. 2):

<u>MVATAAAATSSFFPVPSQSADANFDKAPASLGGIKLKSTSCSRGLQVKAN</u>

<u>AQAPPKINGSSVGFTTSVETVKNDGDMPLPPPP</u>RAFFNQLPDWSMLLTAI

TTVFVAPEKRWTMFDRKSKRPNMLMDSFGLERVVQDGLVFRQSFSIRSYE

ICADRTASIETVMNHVQETSLNQCKSIGLLDDGFGRSPEMCKRDLIWVVT

RMKIMVNRYPTWGDTIEVSTWLSQSGKIGMGRDWLISDCNTGEILVRATS

VYAMMNQKTRRFSKLPHEVRQEFAPHFLDSPPAIEDNDGKLQKFDVKTGD

SIRKGLTPGWYDLDVNQHVSNVKYIGWILESMPTEVLETQELCSLTLEYR

RECGRDSVLESVTSMDPSKVGDRFQYRHLLRLEDGADIMKGRTEWRPKNA

GTNGAISTGKT

XZCP88: Amino acid sequence of a hybrid acyl-ACP thioesterases with the leading/targeting sequence from *Ricinus communis* underlined (SEQ ID NO. 3):

<u>MVATAAAATSSFFPVPSQSADANFDKAPASLGGIKLKSTSCSRGLQVKAN</u>

<u>AQAPPKINGSSVGFTTSVETVKNDGDMPLPPPP</u>RTFINQLPDWSMLLTAI

TTVFVAPEKRWTMFDRKSKRPNMLMDSFGLERVVQDGLVFRQSFSIRSYE

ICADRTASIETVMNHVQETSLNQCKSIGLLDDGFGRSPEMCKRDLIWVVT

RMKIMVNRYPTWGDTIEVSTWLSQSGKIGMGRDWLISDCNTGEILVRATS

VYAMMNQKTRRFSKLPHEVRQEFAPHFLDSPPAIEDNDGKLQKFDVKTGD

SIRKGLTPGWYDLDVNQHVSNVKYIGWILESMPTEVLETQELCSLTLEYR

RECGRDSVLESVTSMDPSKVGDRFQYRHLLRLEDGADIMKGRTEWRPKNA

GTNGAISTGKT

Hybrid TE studies: Various length leading/targeting and/or the C-terminal end sequences from *Ricinus communis* were used to increase free fatty acid production by constructing various combinations of hybrid acyl-ACP thioesterases from *Gossypium hirsutum*. The resulting amino acid sequences of these hybrid Acyl-ACP thioesterases are shown below with the sequence from *Ricinus communis* underlined. The results shown in the table below are the compositions and the sum of all major free fatty acids in the samples at 48 hours, clearly showing that the strains carrying the hybrid acyl-ACP thioesterases accumulated significantly more free fatty acids than that of the strain carrying the same acyl-ACP thioesterase without the leading and/or C-terminal end sequence from *Ricinus communis*. The leading 1-81 amino acids have the most effect, but even much shorter amino terminal sequence are beneficial, as are short C terminal sequences.

The amino acid sequence of the hybrid acyl-ACP thioesterases are shown below with the leading/targeting and/or the C-terminal end sequence from *Ricinus communis* underlined:

```
pXZC016 (SEQ ID NO 4) TE from Gossypium hirsutum.
MVATAVTSAFFPVTSSPDSSDSKNKKLGSIKSKPSVSSGSLQVKANAQAP

PKINGTVASTTPVEGSKNDDGASSPPPRTFINQLPDWSMLLAAITTIFLA

AEKQWMMLDWKPRRPDMVIDPFGIGKIVQDGLVFSQNFSIRSYEIGADQT

ASIETLMNHLQETAINHCRSAGLLGEGFGATPEMCKKNLIWVVTRMQVVV

DRYPTWGDVVQVDTWVSASGKNGMRRDWLVSNSETGEILTRATSVWVMMN

KLTRRLSKIPEEVRGEIEPFFMNSDPVLAEDSQKLVKLDDSTAEHVCKGL

TPKWSDLDVNQHVNNVKYIGWILESAPLPILESHELSALTLEYRRECGRD
```

-continued

SVLQSLTTVSDSNTENAVNVGEFNCQHLLRLDDGAEIVRGRTRWRPKHAK

SSANMDQITAKRA pXZco3 (SEQ ID NO. 5) N terminal from *R. communis*, remainder from *Gossypium hirsutum*:

MVATAAAATSSFFPVPSQSADANFDKAPASLGGIKLKSTSCSRGLQVKAN

AQAPPKINGSSVGFTTSVETVKNDGDMPLPPPPRTFINQLPDWSMLLAAI

TTIFLAAEKQWMMLDWKPRRPDMVIDPFGIGKIVQDGLVFSQNFSIRSYE

IGADQTASIETLMNHLQETAINHCRSAGLLGEGFGATPEMCKKNLIWVVT

RMQVVVDRYPTWGDVVQVDTWVSASGKNGMRRDWLVSNSETGEILTRATS

VWVMMNKLTRRLSKIPEEVRGEIEPFFMNSDPVLAEDSQKLVKLDDSTAE

HVCKGLTPKWSDLDVNQHVNNVKYIGWILESAPLPILESHELSALTLEYR

RECGRDSVLQSLTTVSDSNTENAVNVGEFNCQHLLRLDDGAEIVRGRTRW

RPKHAKSSANMDQITAKRA pXZco5 (SEQ ID NO. 6) N terminal from *R. communis*, remainder from *G. hirsutum*:

MVATAAAATSSFFPVPSQSADANFDKAPASLGGIKLKSTSCSRGLQVKAN

AQAPPKINGTVASTTPVEGSKNDDGASSPPPRTFINQLPDWSMLLAAITT

IFLAAEKQWMMLDWKPRRPDMVIDPFGIGKIVQDGLVFSQNFSIRSYEIG

ADQTASIETLMNHLQETAINHCRSAGLLGEGFGATPEMCKKNLIWVVTRM

QVVVDRYPTWGDVVQVDTWVSASGKNGMRRDWLVSNSETGEILTRATSVW

VMMNKLTRRLSKIPEEVRGEIEPFFMNSDPVLAEDSQKLVKLDDSTAEHV

CKGLTPKWSDLDVNQHVNNVKYIGWILESAPLPILESHELSALTLEYRRE

CGRDSVLQSLTTVSDSNTENAVNVGEFNCQHLLRLDDGAEIVRGRTRWRP

KHAKSSANMDQITAKRA pXZco6 (SEQ ID NO. 7) C terminal from *R. communis*, remainder from *G. hirsutum*:

MVATAVTSAFFPVTSSPDSSDSKNKKLGSIKSKPSVSSGSLQVKANAQAP

PKINGTVASTTPVEGSKNDDGASSPPPRTFINQLPDWSMLLAAITTIFLA

AEKQWMMLDWKPRRPDMVIDPFGIGKIVQDGLVFSQNFSIRSYEIGADQT

ASIETLMNHLQETAINHCRSAGLLGEGFGATPEMCKKNLIWVVTRMQVVV

DRYPTWGDVVQVDTWVSASGKNGMRRDWLVSNSETGEILTRATSVWVMMN

KLTRRLSKIPEEVRGEIEPFFMNSDPVLAEDSQKLVKLDDSTAEHVCKGL

TPKWSDLDVNQHVNNVKYIGWILESAPLPILESHELSALTLEYRRECGRD

SVLQSLTTVSDSNTENAVNVGEFNCQHLLRLDDGAEIVRGRTEWRPKYSS

NFGIMGQIPVESA pXZco7 (SEQ ID NO. 8) C terminal from *R. communis*, remainder from *G. hirsutum*:

MVATAVTSAFFPVTSSPDSSDSKNKKLGSIKSKPSVSSGSLQVKANAQAP

PKINGTVASTTPVEGSKNDDGASSPPPRTFINQLPDWSMLLAAITTIFLA

AEKQWMMLDWKPRRPDMVIDPFGIGKIVQDGLVFSQNFSIRSYEIGADQT

ASIETLMNHLQETAINHCRSAGLLGEGFGATPEMCKKNLIWVVTRMQVVV

DRYPTWGDVVQVDTWVSASGKNGMRRDWLVSNSETGEILTRATSVWVMMN

KLTRRLSKIPEEVRGEIEPFFMNSDPVLAEDSQKLVKLDDSTAEHVCKGL

TPKWSDLDVNQHVNNVKYIGWILESAPLPILESHELSALTLEYRRECGRD

SVLQSLT<u>AVSGNGIGNLGNAGDIECQHLLRLEDGAEIVRGRTEWRPKYSS</u>

<u>NFGIMGQIPVESA</u> pXZco4 (SEQ ID NO. 9) N and C terminals from *R. communis*, remainder from *G. hirsutum*:
<u>MVATAAAATSSFFPVPSQSADANFDKAPASLGGIKLKSTSCSRGLQVKAN</u>

<u>AQAPPKINGSSVGFTTSVETVKNDGDMPLP</u>PPPRTFINQLPDWSMLLAAI

TTIFLAAEKQWMMLDWKPRRPDMVIDPFGIGKIVQDGLVFSQNFSIRSYE

IGADQTASIETLMNHLQETAINHCRSAGLLGEGFGATPEMCKKNLIWVVT

RMQVVVDRYPTWGDVVQVDTWVSASGKNGMRRDWLVSNSETGEILTRATS

VWVMMNKLTRRLSKIPEEVRGEIEPFFMNSDPVLAEDSQKLVKLDDSTAE

HVCKGLTPKWSDLDVNQHVNNVKYIGWILESAPLPILESHELSALTLEYR

RECGRDSVLQSLT<u>AVSGNGIGNLGNAGDIECQHLLRLEDGAEIVRGRTEW</u>

<u>RPKYSSNFGIMGQIPVESA</u> pXZco8 (SEQ ID NO. 10) N and C terminals from *R. communis*, remainder from *G. hirsutum*:
<u>MVATAAAATSSFFPVPSQSADANFDKAPASLGGIKLKSTSCSRGLQVKAN</u>

AQAPPKINGTVASTTPVEGSKNDDGASPPPRTFINQLPDWSMLLAAITT

IFLAAEKQWMMLDWKPRRPDMVIDPFGIGKIVQDGLVFSQNFSIRSYEIG

ADQTASIETLMNHLQETAINHCRSAGLLGEGFGATPEMCKKNLIWVVTRM

QVVVDRYPTWGDVVQVDTWVSASGKNGMRRDWLVSNSETGEILTRATSVW

VMMNKLTRRLSKIPEEVRGEIEPFFMNSDPVLAEDSQKLVKLDDSTAEHV

CKGLTPKWSDLDVNQHVNNVKYIGWILESAPLPILESHELSALTLEYRRE

CGRDSVLQSLT<u>AVSGNGIGNLGNAGDIECQHLLRLEDGAEIVRGRTEWRP</u>

<u>KYSSNFGIMGQIPVESA</u> pXZco9 (SEQ ID NO. 11) N and C terminals from *R. communis*, remainder from *G. hirsutum*:
<u>MVATAAAATSSFFPVPSQSADANFDKAPASLGGIKLKSTSCSRGLQVKAN</u>

AQAPPKINGTVASTTPVEGSKNDDGASPPPRTFINQLPDWSMLLAAITT

IFLAAEKQWMMLDWKPRRPDMVIDPFGIGKIVQDGLVFSQNFSIRSYEIG

ADQTASIETLMNHLQETAINHCRSAGLLGEGFGATPEMCKKNLIWVVTRM

QVVVDRYPTWGDVVQVDTWVSASGKNGMRRDWLVSNSETGEILTRATSVW

VMMNKLTRRLSKIPEEVRGEIEPFFMNSDPVLAEDSQKLVKLDDSTAEHV

CKGLTPKWSDLDVNQHVNNVKYIGWILESAPLPILESHELSALTLEYRRE

CGRDSVLQSLTTVSDSNTENAVNVGEFNCQHLLRLDDGAEIVRGRT<u>EWRP</u>

<u>KYSSNFGIMGQIPVESA</u> pXZco10 (SEQ ID NO. 12) N and C terminals from *R. communis*, remainder from *G. hirsutum*:
<u>MVATAAAATSSFFPVPSQSADANFDKAPASLGGIKLKSTSCSRGLQVKAN</u>

<u>AQAPPKINGSSVGFTTSVETVKNDGDMPLP</u>PPPRTFINQLPDWSMLLAAI

TTIFLAAEKQWMMLDWKPRRPDMVIDPFGIGKIVQDGLVFSQNFSIRSYE

IGADQTASIETLMNHLQETAINHCRSAGLLGEGFGATPEMCKKNLIWVVT

RMQVVVDRYPTWGDVVQVDTWVSASGKNGMRRDWLVSNSETGEILTRATS

VWVMMNKLTRRLSKIPEEVRGEIEPFFMNSDPVLAEDSQKLVKLDDSTAE

HVCKGLTPKWSDLDVNQHVNNVKYIGWILESAPLPILESHELSALTLEYR

RECGRDSVLQSLTTVSDSNTENAVNVGEFNCQHLLRLDDGAEIVRGRTEW

RPKYSSNFGIMGQIPVESA

SEQ ID NO 13: TE from *Ricinus Communis*
MVATAAAATS SFFPVPSQSA DANFDKAPAS LGGIKLKSTS CSRGLQVKAN

AQAPPKINGS SVGFTTSVET VKNDGDMPLP PPPRTFINQL PDWSMLLAAI

TTIFLAAEKQ WMMLDWKPRR PDMLIDPFGI GRIVQDGLIF RQNFSIRSYE

IGADRTASIE TLMNHLQETA LNHVKTAGLL GDGFGSTPEM SKRNLIWVVT

RMQVLVDRYP TWGDVVQVDT WVSKSGKNGM RRDWCVRDSR TGETLTRASS

VWVMMNKLTR RLSKIPEEVR GEIEPYFLNS DPIVDEDSRK LPKLDDSNAD

YVRKGLTPRW SDLDINQHVN NVKYIGWILE SAPLPILESH ELSAITLEYR

RECGRDSVLQ SLTAVSGNGI GNLGNAGDIE CQHLLRLEDG AEIVRGRTEW

RPKYSSNFGI MGQIPVESA

| Strain | C12 | C14 | C16:1 | C16 | C18:1 | C18 | Total |
|---|---|---|---|---|---|---|---|
| ML103(pXZCO16) | 0.0014 | 0.2561 | 0.2931 | 0.1734 | 0.0432 | 0.0123 | 0.7795 |
| ML103(pXZco3) | 0.0034 | 0.9697 | 0.8460 | 0.2613 | 0.0798 | 0.0170 | 2.1771 |
| ML103(pXZco4) | 0.0012 | 0.8555 | 0.7744 | 0.2777 | 0.0857 | 0.0118 | 2.0063 |
| ML103(pXZco5) | 0.0029 | 0.8186 | 0.7233 | 0.2542 | 0.0786 | 0.0176 | 1.8953 |
| ML103(pXZco6) | 0.0027 | 0.9095 | 0.7912 | 0.2745 | 0.0834 | 0.0142 | 2.0755 |
| ML103(pXZco7) | 0.0027 | 0.9492 | 0.8043 | 0.3056 | 0.0929 | 0.0188 | 2.1734 |
| ML103(pXZco8) | 0.0020 | 0.7850 | 0.7003 | 0.3581 | 0.1091 | 0.0179 | 1.9723 |
| ML103(pXZco9) | 0.0035 | 0.7800 | 0.7503 | 0.2785 | 0.0934 | 0.0114 | 1.9170 |
| ML103(pXZco10) | 0.0037 | 0.8401 | 0.7393 | 0.3019 | 0.0889 | 0.0196 | 1.9935 |

ML103(pXZCO16) TE from *Gossypium hirsutum*.
ML103(PXZco3) N terminal from *R. communis*, remainder from *Gossypium hirsutum*.
ML103(PXZco4) N and C terminals from *R. communis*, remainder from *G. hirsutum*.
ML103(PXZco5) N terminal from *R. communis*, remainder from *G. hirsutum*.
ML103(PXZco6) C terminal from *R. communis*, remainder from *G. hirsutum*.
ML103(PXZco7) C terminal from *R. communis*, remainder from *G. hirsutum*.
ML103(PXZco8) N and C terminals from *R. communis*, remainder from *G. hirsutum*.
ML103(PXZco9) N and C terminals from *R. communis*, remainder from *G. hirsutum*.
ML103(PXZco10) N and C terminals from *R. communis*, remainder from *G. hirsutum*.

The following references are incorporated by reference in their entirety:

U.S. Pat. No. 7,326,557.

Davies, H. M., L. Anderson, J. Bleibaum, D. J. Hawkins, C. Fan, A. C. Worrell, and T. A. Voelker. 1993. Fatty acid synthesis genes: Engineering the production of medium chain fatty acids. p. 176-181. In: J. Janick and J. E. Simon (eds.), New crops. Wiley, New York.

Lu, X., H. Vora and C. Khosla. 2008. "Overproduction of free fatty acids in *E. coli*: Implications for biodiesel production." *Metabolic Engineering*. 10: 333-339.

Chin, J. W., Khankal, R., Monroe, C. A., Maranas, C. D., Cirino, P. C., 2009. "Analysis of NADPH supply during xylitol production by engineered *Escherichia coli*." *Biotechnol. Bioeng*. 102(1):209-20.

Sanchez, A. M., Andrews, J., Hussein, I., Bennett, G. N., San, K. Y. 2006. "Effect of overexpression of a soluble pyridine nucleotide transhydrogenase (UdhA) on the production of poly(3-hydroxybutyrate) in *Escherichia coli*." *Biotechnol. Prog*. 22(2):420-5.

What is claimed is:

1. A recombinant microorganism comprising at least one overexpressed hybrid acyl-ACP thioesterase, and wherein i) at least one protein from the tricarboxylic acid cycle is reduced, or ii) at least one protein from glycolysis pathway is reduced, or both i) and ii) are reduced.

2. The microorganism of claim 1, wherein said at least one protein from the tricarboxylic acid cycle is selected from the group consisting of aconitase, isocitrate dehydrogenase, α-ketoglutarate dehydrogenase, succinyl-coA synthetase, succinic dehydrogenase, fumarase, malate dehydrogenase, and citrate synthase.

3. The microorganism of claim 1, wherein said at least one protein from the tricarboxylic acid cycle is succinyl-CoA synthetase.

4. The microorganism of claim 1, further comprising at least one further modification selected from the group consisting of i) overexpressed malonyl coenzyme A-acyl carrier protein transacylase, ii) overexpressed transhydrogenase, iii) moderately overexpressed acetyl-CoA carboxylase, iv) overexpressed NAD kinase and v) reduced activity of endogenous fatty acyl-CoA synthetase.

5. The microorganism of claim 4, wherein said transhydrogenase is a soluble pyridine nucleotide transhydrogenase.

6. A microorganism comprising an overexpressed hybrid acyl-ACP thioesterase comprising amino acids 1-40 or 397-419 of the acyl-ACP thioesterase from *Ricinus communis* (SEQ ID NO 13) or a 90% homolog thereof that is operably coupled to the carboxyl or amino region of a second thioesterase from another species.

7. A microorganism comprising an overexpressed hybrid acyl-ACP thioesterase comprising a 95% homolog to:
   i) amino acid 1 to amino acid 40 of SEQ ID NO 13, or
   ii) amino acid 397 to amino acid 419 of SEQ ID NO 13, or
   iii) both i) and ii),
   operably fused to the remainder of an acyl-ACP thioesterase of another species.

8. A gene encoding the hybrid thioesterase comprising a 90-100% homolog of amino acid 1 to amino acid 40 of SEQ ID NO. 13 operably fused to the amino region of a second thioesterase.

* * * * *

SEQUENCE LISTING

<160> NUMBER OF SEQ ID NOS: 13

<210> SEQ ID NO 1
<211> LENGTH: 419
<212> TYPE: PRT
<213> ORGANISM: Artificial Sequence
<220> FEATURE:
<223> OTHER INFORMATION: hybrid acyl-ACP thioesterases

<400> SEQUENCE: 1

```
Met Val Ala Thr Ala Ala Ala Thr Ser Ser Phe Phe Pro Val Pro
1               5                   10                  15

Ser Gln Ser Ala Asp Ala Asn Phe Asp Lys Ala Pro Ala Ser Leu Gly
            20                  25                  30

Gly Ile Lys Leu Lys Ser Thr Ser Cys Ser Arg Gly Leu Gln Val Lys
        35                  40                  45

Ala Asn Ala Gln Ala Pro Pro Lys Ile Asn Gly Ser Ser Val Gly Phe
    50                  55                  60

Thr Thr Ser Val Glu Thr Val Lys Asn Asp Gly Asp Met Pro Leu Pro
65                  70                  75                  80

Pro Pro Pro Arg Thr Met Ile Asn Gln Leu Pro Asp Trp Ser Met Leu
                85                  90                  95

Leu Ala Ala Ile Thr Thr Ile Phe Leu Ala Ala Glu Lys Gln Trp Met
                100                 105                 110

Met Leu Asp Trp Lys Pro Arg Arg Pro Asp Met Ile Ile Asp Ser Phe
            115                 120                 125

Gly Leu Gly Lys Ile Val Gln Asp Gly Leu Val Phe Arg Gln Asn Phe
        130                 135                 140

Ser Ile Arg Ser Tyr Glu Ile Gly Ala Asp Arg Thr Ala Ser Val Glu
145                 150                 155                 160

Thr Met Met Asn His Leu Gln Glu Thr Ala Leu Asn His Val Arg Ala
                165                 170                 175

Ala Gly Leu Met Ala Asp Gly Phe Gly Ala Thr Pro Glu Met Ser Lys
                180                 185                 190

Arg Asn Leu Ile Trp Val Val Thr Lys Met Gln Val Leu Val Asp Arg
            195                 200                 205

Tyr Pro Lys Trp Gly Asp Val Val Gln Val Glu Thr Trp Ile Ala Ala
        210                 215                 220

Tyr Gly Lys Asn Cys Met Arg Arg Asp Trp Phe Val Arg Asp Cys Lys
225                 230                 235                 240

Thr Gly Asp Ile Ile Thr Arg Ala Ser Ser Val Trp Val Met Met Asn
                245                 250                 255

Lys Glu Thr Arg Arg Leu Ser Lys Ile Pro His Glu Val Arg Cys Glu
                260                 265                 270

Ile Gly Ser Tyr Phe Val Asp Ser Pro Pro Val Leu Ala Glu Asp Ser
            275                 280                 285

Arg Lys Leu Arg Lys Leu Asp Glu Ser Thr Ala Asp Tyr Ile Cys Thr
        290                 295                 300

Gly Leu Lys Pro Arg Trp Ser Asp Leu Asp Val Asn Gln His Val Asn
305                 310                 315                 320

Asn Val Lys Tyr Ile Gly Trp Ile Leu Glu Thr Ala Pro Gln Leu Ile
                325                 330                 335

Leu Glu Ser His Glu Leu Cys Gly Met Thr Leu Glu Tyr Arg Arg Glu
                340                 345                 350

Cys Gly Lys Asp Ser Val Leu Gln Ser Met Thr Ala Val Ser Gly Gly
```

```
                355                 360                 365
Ala Ile Gly Gly Leu Val Asp Pro Gly Tyr Val Glu Cys Gln His Leu
            370                 375                 380

Leu Arg Leu Glu Asp Gly Ala Glu Ile Val Lys Ala Arg Thr His Trp
385                 390                 395                 400

Arg Pro Lys Tyr Ala Asn Cys Leu Gly Ser His Gly Gln Leu Pro Ala
                405                 410                 415

Glu Ser Ala

<210> SEQ ID NO 2
<211> LENGTH: 177
<212> TYPE: PRT
<213> ORGANISM: Artificial Sequence
<220> FEATURE:
<223> OTHER INFORMATION: hybrid acyl-ACP thioesterases

<400> SEQUENCE: 2

Met Val Ala Thr Ala Ala Ala Thr Ser Ser Phe Phe Pro Val Pro
1               5                   10                  15

Ser Gln Ser Ala Asp Ala Asn Phe Asp Lys Ala Pro Ala Ser Leu Gly
                20                  25                  30

Gly Ile Lys Leu Lys Ser Thr Ser Cys Ser Arg Gly Leu Gln Val Lys
            35                  40                  45

Ala Asn Ala Gln Ala Pro Pro Lys Ile Asn Gly Ser Ser Val Gly Phe
    50                  55                  60

Thr Thr Ser Val Glu Thr Val Lys Asn Asp Gly Asp Met Pro Leu Pro
65                  70                  75                  80

Pro Pro Pro Arg Ala Phe Phe Asn Gln Leu Pro Asp Trp Ser Met Leu
                85                  90                  95

Leu Thr Ala Ile Thr Thr Val Phe Val Ala Pro Glu Lys Arg Trp Thr
            100                 105                 110

Met Phe Asp Arg Lys Ser Lys Arg Pro Asn Met Leu Met Asp Ser Phe
        115                 120                 125

Gly Leu Glu Arg Val Val Gln Asp Gly Leu Val Phe Arg Gln Ser Phe
    130                 135                 140

Ser Ile Arg Ser Tyr Glu Ile Cys Ala Asp Arg Thr Ala Ser Ile Glu
145                 150                 155                 160

Thr Val Met Asn His Val Gln Glu Thr Ser Leu Asn Gln Cys Lys Ser
                165                 170                 175

Ile

<210> SEQ ID NO 3
<211> LENGTH: 411
<212> TYPE: PRT
<213> ORGANISM: Artificial Sequence
<220> FEATURE:
<223> OTHER INFORMATION: hybrid acyl-ACP thioesterases

<400> SEQUENCE: 3

Met Val Ala Thr Ala Ala Ala Thr Ser Ser Phe Phe Pro Val Pro
1               5                   10                  15

Ser Gln Ser Ala Asp Ala Asn Phe Asp Lys Ala Pro Ala Ser Leu Gly
                20                  25                  30

Gly Ile Lys Leu Lys Ser Thr Ser Cys Ser Arg Gly Leu Gln Val Lys
            35                  40                  45

Ala Asn Ala Gln Ala Pro Pro Lys Ile Asn Gly Ser Ser Val Gly Phe
    50                  55                  60
```

Thr Thr Ser Val Glu Thr Val Lys Asn Asp Gly Asp Met Pro Leu Pro
 65                  70                  75                  80

Pro Pro Pro Arg Thr Phe Ile Asn Gln Leu Pro Asp Trp Ser Met Leu
                 85                  90                  95

Leu Thr Ala Ile Thr Thr Val Phe Val Ala Pro Glu Lys Arg Trp Thr
            100                 105                 110

Met Phe Asp Arg Lys Ser Lys Arg Pro Asn Met Leu Met Asp Ser Phe
        115                 120                 125

Gly Leu Glu Arg Val Val Gln Asp Gly Leu Val Phe Arg Gln Ser Phe
    130                 135                 140

Ser Ile Arg Ser Tyr Glu Ile Cys Ala Asp Arg Thr Ala Ser Ile Glu
145                 150                 155                 160

Thr Val Met Asn His Val Gln Glu Thr Ser Leu Asn Gln Cys Lys Ser
                165                 170                 175

Ile Gly Leu Leu Asp Asp Gly Phe Gly Arg Ser Pro Glu Met Cys Lys
            180                 185                 190

Arg Asp Leu Ile Trp Val Val Thr Arg Met Lys Ile Met Val Asn Arg
        195                 200                 205

Tyr Pro Thr Trp Gly Asp Thr Ile Glu Val Ser Thr Trp Leu Ser Gln
    210                 215                 220

Ser Gly Lys Ile Gly Met Gly Arg Asp Trp Leu Ile Ser Asp Cys Asn
225                 230                 235                 240

Thr Gly Glu Ile Leu Val Arg Ala Thr Ser Val Tyr Ala Met Met Asn
                245                 250                 255

Gln Lys Thr Arg Arg Phe Ser Lys Leu Pro His Glu Val Arg Gln Glu
            260                 265                 270

Phe Ala Pro His Phe Leu Asp Ser Pro Pro Ala Ile Glu Asp Asn Asp
        275                 280                 285

Gly Lys Leu Gln Lys Phe Asp Val Lys Thr Gly Asp Ser Ile Arg Lys
    290                 295                 300

Gly Leu Thr Pro Gly Trp Tyr Asp Leu Asp Val Asn Gln His Val Ser
305                 310                 315                 320

Asn Val Lys Tyr Ile Gly Trp Ile Leu Glu Ser Met Pro Thr Glu Val
                325                 330                 335

Leu Glu Thr Gln Glu Leu Cys Ser Leu Thr Leu Glu Tyr Arg Arg Glu
            340                 345                 350

Cys Gly Arg Asp Ser Val Leu Glu Ser Val Thr Ser Met Asp Pro Ser
        355                 360                 365

Lys Val Gly Asp Arg Phe Gln Tyr Arg His Leu Leu Arg Leu Glu Asp
    370                 375                 380

Gly Ala Asp Ile Met Lys Gly Arg Thr Glu Trp Arg Pro Lys Asn Ala
385                 390                 395                 400

Gly Thr Asn Gly Ala Ile Ser Thr Gly Lys Thr
                405                 410

<210> SEQ ID NO 4
<211> LENGTH: 413
<212> TYPE: PRT
<213> ORGANISM: Artificial Sequence
<220> FEATURE:
<223> OTHER INFORMATION: Hybrid acyl-ACP thioesterases, TE from
      Gossypium hirsutum C-terminal end sequence from Ricinus communis

<400> SEQUENCE: 4

Met Val Ala Thr Ala Val Thr Ser Ala Phe Phe Pro Val Thr Ser Ser

```
  1               5                  10                 15
Pro Asp Ser Ser Asp Ser Lys Asn Lys Lys Leu Gly Ser Ile Lys Ser
                 20              25                 30

Lys Pro Ser Val Ser Ser Gly Ser Leu Gln Val Lys Ala Asn Ala Gln
             35              40                 45

Ala Pro Pro Lys Ile Asn Gly Thr Val Ala Ser Thr Thr Pro Val Glu
         50                  55              60

Gly Ser Lys Asn Asp Asp Gly Ala Ser Ser Pro Pro Arg Thr Phe
 65              70                  75                  80

Ile Asn Gln Leu Pro Asp Trp Ser Met Leu Leu Ala Ala Ile Thr Thr
                 85              90              95

Ile Phe Leu Ala Ala Glu Lys Gln Trp Met Met Leu Asp Trp Lys Pro
             100             105             110

Arg Arg Pro Asp Met Val Ile Asp Pro Phe Gly Ile Gly Lys Ile Val
             115             120             125

Gln Asp Gly Leu Val Phe Ser Gln Asn Phe Ser Ile Arg Ser Tyr Glu
         130             135             140

Ile Gly Ala Asp Gln Thr Ala Ser Ile Glu Thr Leu Met Asn His Leu
145             150             155             160

Gln Glu Thr Ala Ile Asn His Cys Arg Ser Ala Gly Leu Leu Gly Glu
                 165             170             175

Gly Phe Gly Ala Thr Pro Glu Met Cys Lys Lys Asn Leu Ile Trp Val
             180             185             190

Val Thr Arg Met Gln Val Val Asp Arg Tyr Pro Thr Trp Gly Asp
             195             200             205

Val Val Gln Val Asp Thr Trp Val Ser Ala Ser Gly Lys Asn Gly Met
 210             215             220

Arg Arg Asp Trp Leu Val Ser Asn Ser Glu Thr Gly Glu Ile Leu Thr
225             230             235             240

Arg Ala Thr Ser Val Trp Val Met Met Asn Lys Leu Thr Arg Arg Leu
             245             250             255

Ser Lys Ile Pro Glu Glu Val Arg Gly Glu Ile Glu Pro Phe Phe Met
             260             265             270

Asn Ser Asp Pro Val Leu Ala Glu Asp Ser Gln Lys Leu Val Lys Leu
             275             280             285

Asp Asp Ser Thr Ala Glu His Val Cys Lys Gly Leu Thr Pro Lys Trp
             290             295             300

Ser Asp Leu Asp Val Asn Gln His Val Asn Asn Val Lys Tyr Ile Gly
305             310             315             320

Trp Ile Leu Glu Ser Ala Pro Leu Pro Ile Leu Glu Ser His Glu Leu
             325             330             335

Ser Ala Leu Thr Leu Glu Tyr Arg Arg Glu Cys Gly Arg Asp Ser Val
             340             345             350

Leu Gln Ser Leu Thr Thr Val Ser Asp Ser Asn Thr Glu Asn Ala Val
             355             360             365

Asn Val Gly Glu Phe Asn Cys Gln His Leu Leu Arg Leu Asp Asp Gly
             370             375             380

Ala Glu Ile Val Arg Gly Arg Thr Arg Trp Arg Pro Lys His Ala Lys
385             390             395             400

Ser Ser Ala Asn Met Asp Gln Ile Thr Ala Lys Arg Ala
             405             410

<210> SEQ ID NO 5
```

<211> LENGTH: 419
<212> TYPE: PRT
<213> ORGANISM: Artificial Sequence
<220> FEATURE:
<223> OTHER INFORMATION: N terminal from R. communis, remainder from Gossypium hirsutum

<400> SEQUENCE: 5

```
Met Val Ala Thr Ala Ala Ala Thr Ser Ser

```
              370                 375                 380
Leu Arg Leu Asp Asp Gly Ala Glu Ile Val Arg Gly Arg Thr Arg Trp
385                 390                 395                 400

Arg Pro Lys His Ala Lys Ser Ser Ala Asn Met Asp Gln Ile Thr Ala
                405                 410                 415

Lys Arg Ala

<210> SEQ ID NO 6
<211> LENGTH: 417
<212> TYPE: PRT
<213> ORGANISM: Artificial Sequence
<220> FEATURE:
<223> OTHER INFORMATION: N terminal from R. communis, rem

```
305                 310                 315                 320
Lys Tyr Ile Gly Trp Ile Leu Glu Ser Ala Pro Leu Pro Ile Leu Glu
                325                 330                 335

Ser His Glu Leu Ser Ala Leu Thr Leu Glu Tyr Arg Arg Glu Cys Gly
            340                 345                 350

Arg Asp Ser Val Leu Gln Ser Leu Thr Thr Val Ser Asp Ser Asn Thr
        355                 360                 365

Glu Asn Ala Val Asn Val Gly Glu Phe Asn Cys Gln His Leu Leu Arg
    370                 375                 380

Leu Asp Asp Gly Ala Glu Ile Val Arg Gly Arg Thr Arg Trp Arg Pro
385                 390                 395                 400

Lys His Ala Lys Ser Ser Ala Asn Met Asp Gln Ile Thr Ala Lys Arg
                405                 410                 415

Ala

<210> SEQ ID NO 7
<211> LENGTH: 413
<212> TYPE: PRT
<213> ORGANISM: Artificial Sequence
<220> FEATURE:
<223> OTHER INFORMATION: C terminal from R. communis, remainder from G.
      hirsutum

<400> SEQUENCE: 7

Met Val Ala Thr Ala Val Thr Ser Ala Phe Phe Pro Val Thr Ser Ser
1               5                   10                  15

Pro Asp Ser Ser Asp Ser Lys Asn Lys Lys Leu Gly Ser Ile Lys Ser
            20                  25                  30

Lys Pro Ser Val Ser Ser Gly Ser Leu Gln Val Lys Ala Asn Ala Gln
        35                  40                  45

Ala Pro Pro Lys Ile Asn Gly Thr Val Ala Ser Thr Thr Pro Val Glu
    50                  55                  60

Gly Ser Lys Asn Asp Asp Gly Ala Ser Ser Pro Pro Arg Thr Phe
65                  70                  75                  80

Ile Asn Gln Leu Pro Asp Trp Ser Met Leu Leu Ala Ala Ile Thr Thr
                85                  90                  95

Ile Phe Leu Ala Ala Glu Lys Gln Trp Met Met Leu Asp Trp Lys Pro
            100                 105                 110

Arg Arg Pro Asp Met Val Ile Asp Pro Phe Gly Ile Gly Lys Ile Val
        115                 120                 125

Gln Asp Gly Leu Val Phe Ser Gln Asn Phe Ser Ile Arg Ser Tyr Glu
    130                 135                 140

Ile Gly Ala Asp Gln Thr Ala Ser Ile Glu Thr Leu Met Asn His Leu
145                 150                 155                 160

Gln Glu Thr Ala Ile Asn His Cys Arg Ser Ala Gly Leu Leu Gly Glu
                165                 170                 175

Gly Phe Gly Ala Thr Pro Glu Met Cys Lys Lys Asn Leu Ile Trp Val
            180                 185                 190

Val Thr Arg Met Gln Val Val Asp Arg Tyr Pro Thr Trp Gly Asp
        195                 200                 205

Val Val Gln Val Asp Thr Trp Val Ser Ala Ser Gly Lys Asn Gly Met
    210                 215                 220

Arg Arg Asp Trp Leu Val Ser Asn Ser Glu Thr Gly Glu Ile Leu Thr
225                 230                 235                 240

Arg Ala Thr Ser Val Trp Val Met Met Asn Lys Leu Thr Arg Arg Leu
```

```
                     245                 250                 255
Ser Lys Ile Pro Glu Glu Val Arg Gly Glu Ile Glu Pro Phe Phe Met
                260                 265                 270

Asn Ser Asp Pro Val Leu Ala Glu Asp Ser Gln Lys Leu Val Lys Leu
            275                 280                 285

Asp Asp Ser Thr Ala Glu His Val Cys Lys Gly Leu Thr Pro Lys Trp
        290                 295                 300

Ser Asp Leu Asp Val Asn Gln His Val Asn Asn Val Lys Tyr Ile Gly
305                 310                 315                 320

Trp Ile Leu Glu Ser Ala Pro Leu Pro Ile Leu Glu Ser His Glu Leu
                325                 330                 335

Ser Ala Leu Thr Leu Glu Tyr Arg Arg Glu Cys Gly Arg Asp Ser Val
            340                 345                 350

Leu Gln Ser Leu Thr Thr Val Ser Asp Ser Asn Thr Glu Asn Ala Val
        355                 360                 365

Asn Val Gly Glu Phe Asn Cys Gln His Leu Leu Arg Leu Asp Asp Gly
    370                 375                 380

Ala Glu Ile Val Arg Gly Arg Thr Glu Trp Arg Pro Lys Tyr Ser Ser
385                 390                 395                 400

Asn Phe Gly Ile Met Gly Gln Ile Pro Val Glu Ser Ala
                405                 410
```

<210> SEQ ID NO 8
<211> LENGTH: 413
<212> TYPE: PRT
<213> ORGANISM: Artificial Sequence
<220> FEATURE:
<223> OTHER INFORMATION: C terminal from R. communis, remainder from G. hirsutum

<400> SEQUENCE: 8

```
Met Val Ala Thr Ala Val Thr Ser Ala Phe Phe Pro Val Thr Ser Ser
1               5                   10                  15

Pro Asp Ser Ser Asp Ser Lys Asn Lys Lys Leu Gly Ser Ile Lys Ser
            20                  25                  30

Lys Pro Ser Val Ser Ser Gly Ser Leu Gln Val Lys Ala Asn Ala Gln
        35                  40                  45

Ala Pro Pro Lys Ile Asn Gly Thr Val Ala Ser Thr Thr Pro Val Glu
    50                  55                  60

Gly Ser Lys Asn Asp Asp Gly Ala Ser Ser Pro Pro Arg Thr Phe
65                  70                  75                  80

Ile Asn Gln Leu Pro Asp Trp Ser Met Leu Leu Ala Ala Ile Thr Thr
                85                  90                  95

Ile Phe Leu Ala Ala Glu Lys Gln Trp Met Met Leu Asp Trp Lys Pro
            100                 105                 110

Arg Arg Pro Asp Met Val Ile Asp Pro Phe Gly Ile Gly Lys Ile Val
        115                 120                 125

Gln Asp Gly Leu Val Phe Ser Gln Asn Phe Ser Ile Arg Ser Tyr Glu
    130                 135                 140

Ile Gly Ala Asp Gln Thr Ala Ser Ile Glu Thr Leu Met Asn His Leu
145                 150                 155                 160

Gln Glu Thr Ala Ile Asn His Cys Arg Ser Ala Gly Leu Leu Gly Glu
                165                 170                 175

Gly Phe Gly Ala Thr Pro Glu Met Cys Lys Lys Asn Leu Ile Trp Val
            180                 185                 190
```

```
Val Thr Arg Met Gln Val Val Asp Arg Tyr Pro Thr Trp Gly Asp
            195                 200                 205

Val Val Gln Val Asp Thr Trp Val Ser Ala Ser Gly Lys Asn Gly Met
    210                 215                 220

Arg Arg Asp Trp Leu Val Ser Asn Ser Glu Thr Gly Glu Ile Leu Thr
225                 230                 235                 240

Arg Ala Thr Ser Val Trp Val Met Met Asn Lys Leu Thr Arg Arg Leu
                245                 250                 255

Ser Lys Ile Pro Glu Glu Val Arg Gly Glu Ile Glu Pro Phe Phe Met
            260                 265                 270

Asn Ser Asp Pro Val Leu Ala Glu Asp Ser Gln Lys Leu Val Lys Leu
        275                 280                 285

Asp Asp Ser Thr Ala Glu His Val Cys Lys Gly Leu Thr Pro Lys Trp
    290                 295                 300

Ser Asp Leu Asp Val Asn Gln His Val Asn Asn Val Lys Tyr Ile Gly
305                 310                 315                 320

Trp Ile Leu Glu Ser Ala Pro Leu Pro Ile Leu Glu Ser His Glu Leu
                325                 330                 335

Ser Ala Leu Thr Leu Glu Tyr Arg Arg Glu Cys Gly Arg Asp Ser Val
            340                 345                 350

Leu Gln Ser Leu Thr Ala Val Ser Gly Asn Gly Ile Gly Asn Leu Gly
        355                 360                 365

Asn Ala Gly Asp Ile Glu Cys Gln His Leu Leu Arg Leu Glu Asp Gly
    370                 375                 380

Ala Glu Ile Val Arg Gly Arg Thr Glu Trp Arg Pro Lys Tyr Ser Ser
385                 390                 395                 400

Asn Phe Gly Ile Met Gly Gln Ile Pro Val Glu Ser Ala
                405                 410

<210> SEQ ID NO 9
<211> LENGTH: 419
<212> TYPE: PRT
<213> ORGANISM: Artificial Sequence
<220> FEATURE:
<223> OTHER INFORMATION: N and C terminals from R. communis, remainder
      from G. hirsutum

<400> SEQUENCE: 9

Met Val Ala Thr Ala Ala Ala Thr Ser Ser Phe Phe Pro Val Pro
1               5                   10                  15

Ser Gln Ser Ala Asp Ala Asn Phe Asp Lys Ala Pro Ala Ser Leu Gly
                20                  25                  30

Gly Ile Lys Leu Lys Ser Thr Ser Cys Ser Arg Gly Leu Gln Val Lys
            35                  40                  45

Ala Asn Ala Gln Ala Pro Pro Lys Ile Asn Gly Ser Ser Val Gly Phe
        50                  55                  60

Thr Thr Ser Val Glu Thr Val Lys Asn Asp Gly Asp Met Pro Leu Pro
65                  70                  75                  80

Pro Pro Pro Arg Thr Phe Ile Asn Gln Leu Pro Asp Trp Ser Met Leu
                85                  90                  95

Leu Ala Ala Ile Thr Thr Ile Phe Leu Ala Ala Glu Lys Gln Trp Met
            100                 105                 110

Met Leu Asp Trp Lys Pro Arg Arg Pro Asp Met Val Ile Asp Pro Phe
        115                 120                 125

Gly Ile Gly Lys Ile Val Gln Asp Gly Leu Val Phe Ser Gln Asn Phe
    130                 135                 140
```

```
Ser Ile Arg Ser Tyr Glu Ile Gly Ala Asp Gln Thr Ala Ser Ile Glu
145                 150                 155                 160

Thr Leu Met Asn His Leu Gln Glu Thr Ala Ile Asn His Cys Arg Ser
            165                 170                 175

Ala Gly Leu Leu Gly Glu Gly Phe Gly Ala Thr Pro Glu Met Cys Lys
        180                 185                 190

Lys Asn Leu Ile Trp Val Val Thr Arg Met Gln Val Val Asp Arg
        195                 200                 205

Tyr Pro Thr Trp Gly Asp Val Gln Val Asp Thr Trp Val Ser Ala
    210                 215                 220

Ser Gly Lys Asn Gly Met Arg Arg Asp Trp Leu Val Ser Asn Ser Glu
225                 230                 235                 240

Thr Gly Glu Ile Leu Thr Arg Ala Thr Ser Val Trp Val Met Met Asn
            245                 250                 255

Lys Leu Thr Arg Arg Leu Ser Lys Ile Pro Glu Glu Val Arg Gly Glu
        260                 265                 270

Ile Glu Pro Phe Phe Met Asn Ser Asp Pro Val Leu Ala Glu Asp Ser
        275                 280                 285

Gln Lys Leu Val Lys Leu Asp Asp Ser Thr Ala Glu His Val Cys Lys
    290                 295                 300

Gly Leu Thr Pro Lys Trp Ser Asp Leu Asp Val Asn Gln His Val Asn
305                 310                 315                 320

Asn Val Lys Tyr Ile Gly Trp Ile Leu Glu Ser Ala Pro Leu Pro Ile
            325                 330                 335

Leu Glu Ser His Glu Leu Ser Ala Leu Thr Leu Glu Tyr Arg Arg Glu
        340                 345                 350

Cys Gly Arg Asp Ser Val Leu Gln Ser Leu Thr Ala Val Ser Gly Asn
    355                 360                 365

Gly Ile Gly Asn Leu Gly Asn Ala Gly Asp Ile Glu Cys Gln His Leu
    370                 375                 380

Leu Arg Leu Glu Asp Gly Ala Glu Ile Val Arg Gly Arg Thr Glu Trp
385                 390                 395                 400

Arg Pro Lys Tyr Ser Ser Asn Phe Gly Ile Met Gly Gln Ile Pro Val
            405                 410                 415

Glu Ser Ala

<210> SEQ ID NO 10
<211> LENGTH: 417
<212> TYPE: PRT
<213> ORGANISM: Artificial Sequence
<220> FEATURE:
<223> OTHER INFORMATION: N and C terminals from R. communis, remainder
      from G. hirsutum

<400> S

```
Pro Arg Thr Phe Ile Asn Gln Leu Pro Asp Trp Ser Met Leu Leu Ala
                85                  90                  95

Ala Ile Thr Thr Ile Phe Leu Ala Ala Glu Lys Gln Trp Met Met Leu
            100                 105                 110

Asp Trp Lys Pro Arg Arg Pro Asp Met Val Ile Asp Pro Phe Gly Ile
        115                 120                 125

Gly Lys Ile Val Gln Asp Gly Leu Val Phe Ser Gln Asn Phe Ser Ile
    130                 135                 140

Arg Ser Tyr Glu Ile Gly Ala Asp Gln Thr Ala Ser Ile Glu Thr Leu
145                 150                 155                 160

Met Asn His Leu Gln Glu Thr Ala Ile Asn His Cys Arg Ser Ala Gly
                165                 170                 175

Leu Leu Gly Glu Gly Phe Gly Ala Thr Pro Glu Met Cys Lys Lys Asn
            180                 185                 190

Leu Ile Trp Val Val Thr Arg Met Gln Val Val Asp Arg Tyr Pro
        195                 200                 205

Thr Trp Gly Asp Val Val Gln Val Asp Thr Trp Val Ser Ala Ser Gly
    210                 215                 220

Lys Asn Gly Met Arg Arg Asp Trp Leu Val Ser Asn Ser Glu Thr Gly
225                 230                 235                 240

Glu Ile Leu Thr Arg Ala Thr Ser Val Trp Val Met Met Asn Lys Leu
                245                 250                 255

Thr Arg Arg Leu Ser Lys Ile Pro Glu Glu Val Arg Gly Glu Ile Glu
            260                 265                 270

Pro Phe Phe Met Asn Ser Asp Pro Val Leu Ala Glu Asp Ser Gln Lys
        275                 280                 285

Leu Val Lys Leu Asp Asp Ser Thr Ala Glu His Val Cys Lys Gly Leu
    290                 295                 300

Thr Pro Lys Trp Ser Asp Leu Asp Val Asn Gln His Val Asn Asn Val
305                 310                 315                 320

Lys Tyr Ile Gly Trp Ile Leu Glu Ser Ala Pro Leu Pro Ile Leu Glu
                325                 330                 335

Ser His Glu Leu Ser Ala Leu Thr Leu Glu Tyr Arg Arg Glu Cys Gly
            340                 345                 350

Arg Asp Ser Val Leu Gln Ser Leu Thr Ala Val Ser Gly Asn Gly Ile
        355                 360                 365

Gly Asn Leu Gly Asn Ala Gly Asp Ile Glu Cys Gln His Leu Leu Arg
    370                 375                 380

Leu Glu Asp Gly Ala Glu Ile Val Arg Gly Arg Thr Glu Trp Arg Pro
385                 390                 395                 400

Lys Tyr Ser Ser Asn Phe Gly Ile Met Gly Gln Ile Pro Val Glu Ser
                405                 410                 415

Ala
```

<210> SEQ ID NO 11
<211> LENGTH: 417
<212> TYPE: PRT
<213> ORGANISM: Artificial Sequence
<220> FEATURE:
<223> OTHER INFORMATION: N and C terminals from R. communis, remainder
      from G. hirsutum

<400> SEQUENCE: 11

```
Met Val Ala Thr Ala Ala Ala Thr Ser Ser Phe Phe Pro Val Pro
1               5                   10                  15
```

-continued

Ser Gln Ser Ala Asp Ala Asn Phe Asp Lys Ala Pro Ala Ser Leu Gly
            20                  25                  30

Gly Ile Lys Leu Lys Ser Thr Ser Cys Ser Arg Gly Leu Gln Val Lys
        35                  40                  45

Ala Asn Ala Gln Ala Pro Pro Lys Ile Asn Gly Thr Val Ala Ser Thr
50                  55                  60

Thr Pro Val Glu Gly Ser Lys Asn Asp Asp Gly Ala Ser Ser Pro Pro
65                  70                  75                  80

Pro Arg Thr Phe Ile Asn Gln Leu Pro Asp Trp Ser Met Leu Leu Ala
                85                  90                  95

Ala Ile Thr Thr Ile Phe Leu Ala Ala Glu Lys Gln Trp Met Met Leu
            100                 105                 110

Asp Trp Lys Pro Arg Arg Pro Asp Met Val Ile Asp Pro Phe Gly Ile
        115                 120                 125

Gly Lys Ile Val Gln Asp Gly Leu Val Phe Ser Gln Asn Phe Ser Ile
130                 135                 140

Arg Ser Tyr Glu Ile Gly Ala Asp Gln Thr Ala Ser Ile Glu Thr Leu
145                 150                 155                 160

Met Asn His Leu Gln Glu Thr Ala Ile Asn His Cys Arg Ser Ala Gly
                165                 170                 175

Leu Leu Gly Glu Gly Phe Gly Ala Thr Pro Glu Met Cys Lys Lys Asn
            180                 185                 190

Leu Ile Trp Val Val Thr Arg Met Gln Val Val Asp Arg Tyr Pro
        195                 200                 205

Thr Trp Gly Asp Val Val Gln Val Asp Thr Trp Val Ser Ala Ser Gly
        210                 215                 220

Lys Asn Gly Met Arg Arg Asp Trp Leu Val Ser Asn Ser Glu Thr Gly
225                 230                 235                 240

Glu Ile Leu Thr Arg Ala Thr Ser Val Trp Val Met Met Asn Lys Leu
                245                 250                 255

Thr Arg Arg Leu Ser Lys Ile Pro Glu Glu Val Arg Gly Glu Ile Glu
            260                 265                 270

Pro Phe Phe Met Asn Ser Asp Pro Val Leu Ala Glu Asp Ser Gln Lys
        275                 280                 285

Leu Val Lys Leu Asp Asp Ser Thr Ala Glu His Val Cys Lys Gly Leu
290                 295                 300

Thr Pro Lys Trp Ser Asp Leu Asp Val Asn Gln His Val Asn Asn Val
305                 310                 315                 320

Lys Tyr Ile Gly Trp Ile Leu Glu Ser Ala Pro Leu Pro Ile Leu Glu
                325                 330                 335

Ser His Glu Leu Ser Ala Leu Thr Leu Glu Tyr Arg Arg Glu Cys Gly
            340                 345                 350

Arg Asp Ser Val Leu Gln Ser Leu Thr Thr Val Ser Asp Ser Asn Thr
        355                 360                 365

Glu Asn Ala Val Asn Val Gly Glu Phe Asn Cys Gln His Leu Leu Arg
370                 375                 380

Leu Asp Asp Gly Ala Glu Ile Val Arg Gly Arg Thr Glu Trp Arg Pro
385                 390                 395                 400

Lys Tyr Ser Ser Asn Phe Gly Ile Met Gly Gln Ile Pro Val Glu Ser
                405                 410                 415

Ala

<210> SEQ ID NO 12
<211> LENGTH: 419
<212> TYPE: PRT
<213> ORGANISM: Artificial Sequence
<220> FEATURE:
<223> OTHER INFORMATION: N and C terminals from R. communis, remainder from G. hirsutum

<400> SEQUENCE: 12

```
Met Val Ala Thr Ala Ala Ala Thr Ser Ser Phe Phe Pro Val Pro
 1               5                  10                  15

Ser Gln Ser Ala Asp Ala Asn Phe Asp Lys Ala Pro Ala Ser Leu Gly
                20                  25                  30

Gly Ile Lys Leu Lys Ser Thr Ser Cys Ser Arg Gly Leu Gln Val Lys
            35                  40                  45

Ala Asn Ala Gln Ala Pro Pro Lys Ile Asn Gly Ser Ser Val Gly Phe
        50                  55                  60

Thr Thr Ser Val Glu Thr Val Lys Asn Asp Gly Asp Met Pro Leu Pro
65                  70                  75                  80

Pro Pro Pro Arg Thr Phe Ile Asn Gln Leu Pro Asp Trp Ser Met Leu
                85                  90                  95

Leu Ala Ala Ile Thr Thr Ile Phe Leu Ala Ala Glu Lys Gln Trp Met
                100                 105                 110

Met Leu Asp Trp Lys Pro Arg Arg Pro Asp Met Val Ile Asp Pro Phe
            115                 120                 125

Gly Ile Gly Lys Ile Val Gln Asp Gly Leu Val Phe Ser Gln Asn Phe
        130                 135                 140

Ser Ile Arg Ser Tyr Glu Ile Gly Ala Asp Gln Thr Ala Ser Ile Glu
145                 150                 155                 160

Thr Leu Met Asn His Leu Gln Glu Thr Ala Ile Asn His Cys Arg Ser
                165                 170                 175

Ala Gly Leu Leu Gly Glu Gly Phe Gly Ala Thr Pro Glu Met Cys Lys
            180                 185                 190

Lys Asn Leu Ile Trp Val Val Thr Arg Met Gln Val Val Asp Arg
        195                 200                 205

Tyr Pro Thr Trp Gly Asp Val Val Gln Val Asp Thr Trp Val Ser Ala
210                 215                 220

Ser Gly Lys Asn Gly Met Arg Arg Asp Trp Leu Val Ser Asn Ser Glu
225                 230                 235                 240

Thr Gly Glu Ile Leu Thr Arg Ala Thr Ser Val Trp Val Met Met Asn
                245                 250                 255

Lys Leu Thr Arg Arg Leu Ser Lys Ile Pro Glu Glu Val Arg Gly Glu
            260                 265                 270

Ile Glu Pro Phe Phe Met Asn Ser Asp Pro Val Leu Ala Glu Asp Ser
        275                 280                 285

Gln Lys Leu Val Lys Leu Asp Asp Ser Thr Ala Glu His Val Cys Lys
    290                 295                 300

Gly Leu Thr Pro Lys Trp Ser Asp Leu Asp Val Asn Gln His Val Asn
305                 310                 315                 320

Asn Val Lys Tyr Ile Gly Trp Ile Leu Glu Ser Ala Pro Leu Pro Ile
                325                 330                 335

Leu Glu Ser His Glu Leu Ser Ala Leu Thr Leu Glu Tyr Arg Arg Glu
            340                 345                 350

Cys Gly Arg Asp Ser Val Leu Gln Ser Leu Thr Thr Val Ser Asp Ser
        355                 360                 365
```

-continued

```
Asn Thr Glu Asn Ala Val Asn Val Gly Glu Phe Asn Cys Gln His Leu
    370                 375                 380

Leu Arg Leu Asp Asp Gly Ala Glu Ile Val Arg Gly Arg Thr Glu Trp
385                 390                 395                 400

Arg Pro Lys Tyr Ser Ser Asn Phe Gly Ile Met Gly Gln Ile Pro Val
                405                 410                 415

Glu Ser Ala

<210> SEQ ID NO 13
<211> LENGTH: 419
<212> TYPE: PRT
<213> ORGANISM: Artificial Sequence
<220> FEATURE:
<223> OTHER INFORMATION: TE from Ricinus Communis

<400> SEQUENCE: 13

Met Val Ala Thr Ala Ala Ala Thr Ser Phe Phe Pro Val Pro
1               5                   10                  15

Ser Gln Ser Ala Asp Ala Asn Phe Asp Lys Ala Pro Ala Ser Leu Gly
                20                  25                  30

Gly Ile Lys Leu Lys Ser Thr Ser Cys Ser Arg Gly Leu Gln Val Lys
            35                  40                  45

Ala Asn Ala Gln Ala Pro Pro Lys Ile Asn Gly Ser Ser Val Gly Phe
    50                  55                  60

Thr Thr Ser Val Glu Thr Val Lys Asn Asp Gly Asp Met Pro Leu Pro
65                  70                  75                  80

Pro Pro Pro Arg Thr Phe Ile Asn Gln Leu Pro Asp Trp Ser Met Leu
                85                  90                  95

Leu Ala Ala Ile Thr Thr Ile Phe Leu Ala Ala Glu Lys Gln Trp Met
                100                 105                 110

Met Leu Asp Trp Lys Pro Arg Arg Pro Asp Met Leu Ile Asp Pro Phe
            115                 120                 125

Gly Ile Gly Arg Ile Val Gln Asp Gly Leu Ile Phe Arg Gln Asn Phe
    130                 135                 140

Ser Ile Arg Ser Tyr Glu Ile Gly Ala Asp Arg Thr Ala Ser Ile Glu
145                 150                 155                 160

Thr Leu Met Asn His Leu Gln Glu Thr Ala Leu Asn His Val Lys Thr
                165                 170                 175

Ala Gly Leu Leu Gly Asp Gly Phe Gly Ser Thr Pro Glu Met Ser Lys
            180                 185                 190

Arg Asn Leu Ile Trp Val Val Thr Arg Met Gln Val Leu Val Asp Arg
        195                 200                 205

Tyr Pro Thr Trp Gly Asp Val Val Gln Val Asp Thr Trp Val Ser Lys
    210                 215                 220

Ser Gly Lys Asn Gly Met Arg Arg Asp Trp Cys Val Arg Asp Ser Arg
225                 230                 235                 240

Thr Gly Glu Thr Leu Thr Arg Ala Ser Ser Val Trp Val Met Met Asn
                245                 250                 255

Lys Leu Thr Arg Arg Leu Ser Lys Ile Pro Glu Glu Val Arg Gly Glu
            260                 265                 270

Ile Glu Pro Tyr Phe Leu Asn Ser Asp Pro Ile Val Asp Glu Asp Ser
        275                 280                 285

Arg Lys Leu Pro Lys Leu Asp Asp Ser Asn Ala Asp Tyr Val Arg Lys
    290                 295                 300

Gly Leu Thr Pro Arg Trp Ser Asp Leu Asp Ile Asn Gln His Val Asn
```

-continued

```
305                 310                 315                 320

Asn Val Lys Tyr Ile Gly Trp Ile Leu Glu Ser Ala Pro Leu Pro Ile
            325                 330                 335

Leu Glu Ser His Glu Leu Ser Ala Ile Thr Leu Glu Tyr Arg Arg Glu
            340                 345                 350

Cys Gly Arg Asp Ser Val Leu Gln Ser Leu Thr Ala Val Ser Gly Asn
            355                 360                 365

Gly Ile Gly Asn Leu Gly Asn Ala Gly Asp Ile Glu Cys Gln His Leu
            370                 375                 380

Leu Arg Leu Glu Asp Gly Ala Glu Ile Val Arg Gly Arg Thr Glu Trp
385                 390                 395                 400

Arg Pro Lys Tyr Ser Ser Asn Phe Gly Ile Met Gly Gln Ile Pro Val
            405                 410                 415

Glu Ser Ala
```